United States Patent
DeLuca et al.

(10) Patent No.: US 7,531,527 B2
(45) Date of Patent: May 12, 2009

(54) 2-PROPYLIDENE-19-NOR-VITAMIN D COMPOUNDS

(75) Inventors: Hector F. DeLuca, Deerfield, WI (US);
Rafal R. Sicinski, Warsaw (PL);
Agnieszka Glebocka, Warsaw (PL);
Lori A. Plum, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 11/750,172

(22) Filed: May 17, 2007

(65) Prior Publication Data
US 2007/0213546 A1    Sep. 13, 2007

Related U.S. Application Data

(62) Division of application No. 10/821,479, filed on Apr. 9, 2004, now Pat. No. 7,241,747.

(60) Provisional application No. 60/461,958, filed on Apr. 10, 2003.

(51) Int. Cl.
*A61K 31/59* (2006.01)
*C07C 401/00* (2006.01)
(52) U.S. Cl. ..................... 514/167; 552/653
(58) Field of Classification Search .............. 514/167; 552/653
See application file for complete search history.

(56) References Cited

U.S. PATENT DOCUMENTS

| 4,666,634 A | 5/1987 | Miyamoto et al. |
| 5,086,191 A | 2/1992 | DeLuca et al. |
| 5,237,110 A | 8/1993 | DeLuca et al. |
| 5,246,925 A | 9/1993 | DeLuca et al. |

(Continued)

FOREIGN PATENT DOCUMENTS

EP    0184206    12/1985

(Continued)

OTHER PUBLICATIONS

Baggiolini et al, "Stereochemical Total Synthesis of 1α,25-Dihydroxycholecalciferol and 1β,25-Dihydroxycerocalciferol", Journal of Organic Chemistry, 51, pp. 3098-3108, 1986.

(Continued)

*Primary Examiner*—Sabiha N. Qazi
(74) *Attorney, Agent, or Firm*—Andrus, Sceales, Starke & Sawall, LLP

(57) ABSTRACT

2-propylidene-19-nor-vitamin D compounds are disclosed as well as pharmaceutical uses for these compounds and methods of synthesizing these compounds. These compounds are characterized by high bone calcium mobilization activity and high intestinal calcium transport activity. This results in novel therapeutic agents for the treatment and prophylaxis of diseases where bone formation is desired, particularly osteoporosis, as well as autoimmune diseases such as multiple sclerosis, diabetes mellitus and lupus. These compounds also exhibit pronounced activity in arresting the proliferation of undifferentiated cells and inducing their differentiation to the monocyte thus evidencing use as an anti-cancer agent and for the treatment of skin diseases such as psoriasis. These compounds also increase both breaking strength and crushing strength of bones evidencing use in conjunction with bone replacement surgery such as hip and knee replacements.

6 Claims, 6 Drawing Sheets

U.S. PATENT DOCUMENTS

| | | | |
|---|---|---|---|
| 5,536,713 | A | 7/1996 | DeLuca et al. |
| 5,587,497 | A | 12/1996 | DeLuca et al. |
| 5,817,648 | A | 10/1998 | Kutner et al. |
| 5,843,927 | A | 12/1998 | DeLuca |
| 5,843,928 | A | 12/1998 | DeLuca et al. |
| 5,877,168 | A | 3/1999 | Miyamoto et al. |
| 5,936,133 | A | 8/1999 | DeLuca et al. |
| 5,945,410 | A | 8/1999 | DeLuca et al. |
| 6,392,071 | B1 | 5/2002 | DeLuca et al. |
| 6,537,981 | B2 | 3/2003 | DeLuca et al. |
| 7,053,075 | B2 * | 5/2006 | DeLuca et al. ............. 514/167 |
| 7,241,747 | B2 * | 7/2007 | DeLuca et al. ............. 514/167 |

FOREIGN PATENT DOCUMENTS

| | | |
|---|---|---|
| EP | 0078704 | 4/1987 |
| EP | 0387077 | 9/1990 |
| EP | 0480572 | 4/1992 |
| EP | 0474517 | 11/1992 |
| EP | 0516410 | 12/1992 |
| EP | 1524264 | 5/2001 |
| WO | WO90/09991 | 9/1990 |
| WO | WO96/01811 | 1/1996 |
| WO | WO98/41500 | 9/1998 |
| WO | WO01/92221 | 12/2001 |

OTHER PUBLICATIONS

Bouillon et al, "Biological Activity of Dihydroxylated 19-Nor-(Pre)Vitamin $D_3$", Bioactivity of 19-Nor-Pre D, vol. 8, No. 8, pp. 1009-1015, 1993.

Chemical Abstracts, "Chemistry of Synthetic High Polymers", vol. 110, No. 10, Abstract 110: 82505v, Mar. 6, 1989.

Chemical Abstracts, XP-002066055, vol. 121, No. 21, Nov. 21, 1994.

Fujishima et al, "Synthesis and Biological Activity of 2-Methyl-20-EPI Analogues of 1α,25-Dihydroxyvitamin $D_3$," Bioorganic & Medicinal Chemistry Letters, 8, pp. 2145-2148, 1998.

Kiegiel et al, "Chemical Conversion of Vitamin $D_3$ to its 1,25-Dihydroxy Metabolite", Tetrahedron Letters, vol. 31, No. 43, pp. 6057-60660, 1991.

Konno et al, "A Novel and Practical Route to A-Ring Enyne Synthon for 1α,25-Dihydroxyvitamin $D_3$ Analogs: Synthesis of A-ring Diastereomers of 1α,25-Dihydroxy-Vitamin $D_3$ and 2-Methyl-1,25-Dihydroxyvitamin $D_3$," Bioorganic & Medicinal Chemistry Letters, 8, pp. 151-156, 1998.

Okano et al, "Regulatory Activities of 2β-(3-Hydroxypropoxy)-1α,25-Dihydroxyvitamin $D_3$. A Novel Synthetic Vitamin $D_3$ Derivative on Calcium Metabolism", Biochemical and Biophysical Research Communications, vol. 163, No. 3, pp. 1444-1449, Sep. 29, 1989.

Posner et al, "2-Fluoroalkyl A-Ring Analogs of 1,25-Dihydroxyvitamin $D_3$-Stereocontrolled Total Synthesis via Intramolecular and Intermolecular Diels-Alder Cycloadditions. Preliminary Biological Testing", Journal of Organic Chemistry, 60, pp. 4617-4628, 1995.

Posner et al, "Sterocontrolled Synthesis of a Trihydroxylated A Ring as an Immediate Precursor to 1α,2α,25-Trihydroxyvitamin $D_3$", Journal of Organic Chemistry, 56, pp. 4339-4341, Apr. 15, 1995.

Sarandeses et al, "Synthesis of 1α,25-Dihydroxy-19-Norprevitamin $D_3$", Tetrahedron Letters, pp. 5445-5448, Apr. 1992.

Sicinski et al, "New 1α,25-Dihydroxy-19-Norvitamin $D_3$ Compounds of High Biological Activity: Synthesis and Biological Evaluation of 2-Hydroxymethyl, 2-Methyl, and 2-Methylene Analogues," Journal of Medical Chemistry, 41, pp. 4662-4674, 1998.

Slatopolsky et al, "A New Analog of Calcitriol, 19-Nor-1,25-$(OH)_2$ $D_2$ Suppresses Parathyroid Hormone Secretion in Uremic Rats in the Absence of Hypercalcemia", American Journal of Kidney Disorders, 26(5), 832-60, 1995.

Suhara et al, "Synthesis and Biological Evaluation of Novel 2α-Substituted 1α,25-Dihydroxyvitamin $D_3$ Analogues," Biolorganic & Medicinal Chemistry Letters, 10, pp. 1129-1132, Mar. 16, 2000.

* cited by examiner

2-PROPYLIDENE-19-NOR-VITAMIN D COMPOUNDS

CROSS-REFERENCE TO RELATED APPLICATION

This application is a division of U.S. patent application Ser. No. 10/821,479, filed Apr. 9, 2004 now U.S. Pat. No. 7,241,747. The '479 application claims priority to U.S. Provisional Application No. 60/461,958, filed Apr. 10, 2003.

BACKGROUND OF THE INVENTION

The present invention relates to vitamin D compounds, and more particularly, to 2-alkylidene-19-nor-vitamin D analogs having a substituted propylidene moiety at carbon-2, pharmaceutical uses for such analogs, and a general method for chemically synthesizing such analogs.

The natural hormone $1\alpha,25$-dihydroxyvitamin $D_3$ and its analog in the ergosterol series, i.e. $1\alpha,25$-dihydroxyvitamin $D_2$ are known to be highly potent regulators of calcium homeostasis in animals and humans, and more recently their activity in cellular differentiation has been established, Ostrem et al., Proc. Natl. Acad. Sci. USA, 84, 2610 (1987). Many structural analogs of these metabolites have been prepared and tested, including $1\alpha$-hydroxyvitamin $D_3$, $1\alpha$-hydroxyvitamin $D_2$, various side chain homologated vitamins and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies.

In 1990, a new class of vitamin D analogs was discovered, i.e. the so called 19-nor-vitamin D compounds, characterized by the replacement of the ring A exocyclic methylene group (carbon 19), typical of the vitamin D system, by two hydrogen atoms. Biological testing of such 19-nor-analogs (e.g., $1\alpha,25$-dihydroxy-19-nor-vitamin $D_3$) revealed a selective activity profile with high potency in inducing cellular differentiation, with very low calcium mobilizing activity. Thus, these compounds are potentially useful as therapeutic agents for the treatment of malignancies, or the treatment of various skin disorders. Two different methods of synthesis of such 19-nor-vitamin D analogs have been described (Perlman et al., Tetrahedron Letters 31, 1823 (1990); Perlman et al., Tetrahedron Letters 32, 7663 (1991), and DeLuca et al., U.S. Pat. No. 5,086,191). Few years later, analogs of $1\alpha,25$-dihydroxy-19-norvitamin $D_3$ substituted at the 2-position of its A-ring with hydroxy or alkoxy groups (DeLuca et al., U.S. Pat. No. 5,536,713) were synthesized. It has been established that they exhibit interesting and selective activity profiles. All these studies indicate that binding sites in vitamin D receptors can accommodate different substituents at C-2 in the synthesized vitamin D analogs.

In a continuing effort to explore the 19-nor class of pharmacologically important vitamin D compounds, analogs which are characterized by the transposition of the ring A exocyclic methylene group from carbon 10 (C-10) to carbon 2 (C-2), i.e. 2-methylene-19-nor-vitamin D compounds have been recently synthesized and tested (Sicinski et al., J. Med. Chem., 41, 4662 (1998); Sicinski et al., Steroids 67, 247 (2002); DeLuca et al., U.S. Pat. Nos. 5,843,928, 5,936,133 and 6,382,071). Molecular mechanics studies, performed on these analogs, showed that a change of ring-A conformation can be expected resulting in the "flattening" of the cyclohexanediol ring. From molecular mechanics calculations and NMR studies their A-ring conformational equilibrium was established to be ca. 6:4 in favor of the conformer that has an equatorial $1\alpha$-OH. Introduction of the 2-methylene group into 19-nor-vitamin D carbon skeleton thus changes the character of its ($1\alpha$- and $3\beta$-) A-ring hydroxyls; they are both now in the allylic positions, similarly, as the $1\alpha$-hydroxyl group (crucial for biological activity) in the molecule of the natural hormone, $1\alpha,25$-$(OH)_2D_3$. It was found that $1\alpha,25$-dihydroxy-2-methylene-19-norvitamin D analogs are characterized by significant biological potency, enhanced dramatically in compounds with "unnatural" (20S)-configuration.

Very recently, 2-ethylidene analogs of $1\alpha,25$-dihydroxy-19-norvitamin $D_3$ have been synthesized. Such modification of the ring A results in significant biological potency for the compounds, especially enhanced in the E-geometrical isomers, Sicinski et al., J. Med. Chem., 45, 3366 (2002). Interestingly, it has been established that E-isomers have their A-ring conformational equilibrium considerably shifted to one particular chair form, that possessing $1\alpha$-hydroxyl in an equatorial orientation.

SUMMARY OF THE INVENTION

As a continuation of the search for biologically active 2-alkylidene-19-norvitamin D compounds, analogs which are characterized by the presence of substituted propylidene moiety at C-2 have now been synthesized and tested. Such vitamin D analogs seemed interesting targets because their bulky substituent at C-2 can be expected to cause an even more significant, in comparison with 2-ethylidene group, bias toward one particular A-ring chair conformation. On the other hand, the presence of an oxygen function, located at the terminus of the propylidene fragment, can introduce additional interaction with the vitamin D receptor.

A class of $1\alpha$-hydroxylated vitamin D compounds not known heretofore are the vitamin D isomers having the A-ring exocyclic methylene moiety at C-10 removed and possessing an additional fragment, being a substituted propylidene group, attached to carbon-2. Thus, the present invention is directed toward 2-alkylidene-19-nor-vitamin D analogs having a substituted propylidene moiety at carbon-2, various pharmaceutical uses for these analogs, and a general method for chemically synthesizing these analogs. In particular, the present invention is directed toward the E-isomer and Z-isomer of (20R)-$1\alpha,25$-dihydroxy-2-[3'-hydroxypropylidene]-19-norvitamin $D_3$ as well as the E-isomer and Z-isomer of (20S)-$1\alpha,25$-dihydroxy-2-[3'-hydroxypropylidene]-19-norvitamin $D_3$. Also disclosed is 2-[(3'-methoxymethoxy)propylidene]-19-nor-$1\alpha,25$-$(OH)_2D_3$.

Structurally these novel analogs are characterized by the general formula I shown below:

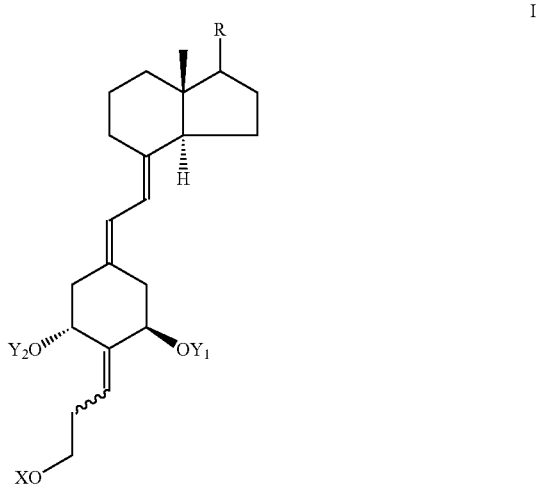

I where $Y_1$ and $Y_2$, which may be the same or different, are each selected from the group consisting of hydrogen and a hydroxy-protecting group, where X may be an alkyl, hydrogen, hydroxy-protecting group, hydroxyalkyl, alkoxyalkyl and aryloxyalkyl, and where the group R represents any of the typical side chains known for vitamin D type compounds.

More specifically, R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below

where the stereochemical center (corresponding to C-20 in steroid numbering) may have the R or S configuration, (i.e. either the natural configuration about carbon 20 or the 20-epi configuration), and where Z is selected from Y, —OY, —$CH_2$OY, —C≡CY and —CH=CHY, where the double bond may have the cis or trans geometry, and where Y is selected from hydrogen, methyl, —$COR^5$ and a radical of the structure:

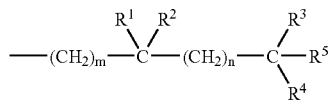

where m and n, independently, represent the integers from 0 to 5, where $R^1$ is selected from hydrogen, deuterium, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from deuterium, deuteroalkyl, hydrogen, fluoro, trifluoromethyl and $C_{1-5}$ alkyl, which may be straight-chain or branched, and optionally, bear a hydroxy or protected-hydroxy substituent, and where $R^1$ and $R^2$, taken together, represent an oxo group, or an alkylidene group, =$CR^2R^3$, or the group —$(CH_2)_p$—, where p is an integer from 2 to 5, and where $R^3$ and $R^4$, taken together, represent an oxo group, or the group —$(CH_2)_q$—, where q is an integer from 2 to 5, and where $R^5$ represents hydrogen, hydroxy, protected hydroxy, or $C_{1-5}$ alkyl and wherein any of the CH-groups at positions 20, 22, or 23 in the side chain may be replaced by a nitrogen atom, or where any of the groups —$CH(CH_3)$—, —$(CH_2)_m$—, $(CH_2)_n$ or —$CR^1R^2$— at positions 20, 22, and 23, respectively, may be replaced by an oxygen or sulfur atom.

The wavy line to the methyl substituent at carbon 20 indicates that carbon 20 may have either the R or S configuration, i.e. the natural configuration (20R) or the unnatural 20-epi configuration (20S).

The wavy line to the carbon 1' indicates possibility of two geometrical isomers of 2-propylidene unit (differing in the orientation of substituents of terminal carbon atoms in the A-ring 1,4-dimethylenecyclohexane fragment).

Specific important examples of side chains with natural 20R-configuration are the structures represented by formulas (a), (b), (c), (d) and (e) below. i.e. the side chain as it occurs in 25-hydroxyvitamin $D_3$ (a); vitamin $D_3$ (b); 25-hydroxyvitamin $D_2$ (c); vitamin $D_2$ (d); and the C-24 epimer of 25-hydroxyvitamin $D_2$ (e).

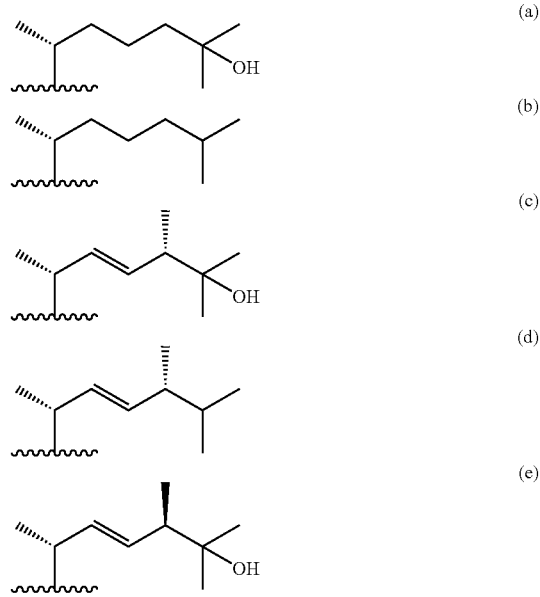

The above novel 2-propylidene-19-nor vitamin D compounds of structure I exhibit a desired, and highly advantageous, pattern of biological activity. These compounds are characterized by relatively high intestinal calcium transport activity, i.e. similar to that of 1α,25-dihydroxyvitamin $D_3$, while also exhibiting relatively high activity, as compared to 1α,25-dihydroxyvitamin $D_3$, in their ability to mobilize calcium from bone. Hence, these compounds are highly specific in their calcemic activity. Their preferential activity on intestinal calcium transport and calcium mobilizing activity allows the in vivo administration of these compounds for the treatment and prophylaxis of metabolic bone diseases where bone loss is a major concern. Because of their preferential calcemic activity on gut calcium transport and on bone, these compounds would be preferred therapeutic agents for the treatment and prophylaxis of diseases where bone formation is desired, such as osteoporosis, especially low bone turnover osteoporosis, steroid induced osteoporosis, senile osteoporosis or postmenopausal osteoporosis, as well as osteomalacia and renal osteodystrophy. The compounds may be administered transdermally, orally or parenterally. The compounds may be present in a pharmaceutical composition in an amount from about 0.01 μg/gm to about 100 μg/gm of the composition, preferably from about 0.1 μg/gm to about 50 μg/gm of the composition, and may be administered in dosages of from about 0.01 μg/day to about 100 μg/day, preferably from about 0.1 μg/day to about 50 μg/day.

The compounds of the invention are also especially suited for treatment and prophylaxis of human disorders which are characterized by an imbalance in the immune system, e.g. in autoimmune diseases, including multiple sclerosis, diabetes mellitus, lupus, host versus graft reaction, and rejection of transplants; and additionally for the treatment and prophylaxis of inflammatory diseases, such as rheumatoid arthritis, asthma, and inflammatory bowel diseases such as Crohn's disease or ulcerative colitis, as well as the improvement of bone fracture healing and improved bone grafts. It has also been discovered that these compounds increase breaking strength (cortical strength) as well as crushing strength (trabecular strength) of bones. Thus, these compounds could also be used in conjunction with bone replacement procedures such as hip replacements, knee replacements, and the like. Acne, alopecia, skin conditions such as dry skin (lack of dermal hydration), undue skin slackness (insufficient skin firmness), insufficient sebum secretion and wrinkles, and hypertension are other conditions which may be treated with the compounds of the invention.

The above compounds are also characterized by high cell differentiation activity. Thus, these compounds also provide therapeutic agents for the treatment of psoriasis, or as an anti-cancer agent, especially against leukemia, colon cancer, breast cancer, skin cancer and prostate cancer. The compounds may be present in a composition to treat psoriasis in an amount from about 0.01 μg/gm to about 100 μg/gm of the composition, preferably from about 0.1 μg/gm to about 50 μg/gm of the composition, and may be administered topically, transdermally, orally or parenterally in dosages of from about 0.01 μg/day to about 100 μg/day, preferably from about 0.1 μg/day to about 50 μg/day.

In particular, the E-isomer and Z-isomer of both the (20R) and (20S) isomers of 1α,25-dihydroxy-2-[3'-hydroxypropylidene]-19-norvitamin $D_3$ have been synthesized and their binding, transcriptional, calcemic (both intestinal calcium transport and bone calcium mobilization) and differentiation activities determined. Structurally, the E-isomer of this (20R) analog is characterized by the general formula Ia shown below and is referred to herein as "1AGR":

Structurally, the E-isomer of this (20S) analog is characterized by the general formula Ic shown below and is referred to herein as "1AGS":

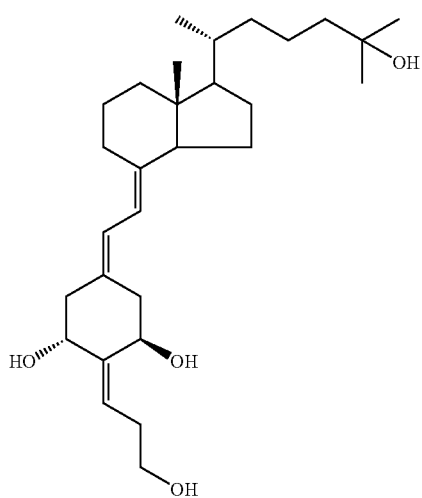

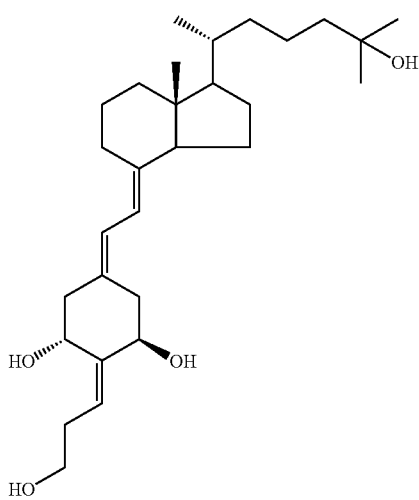

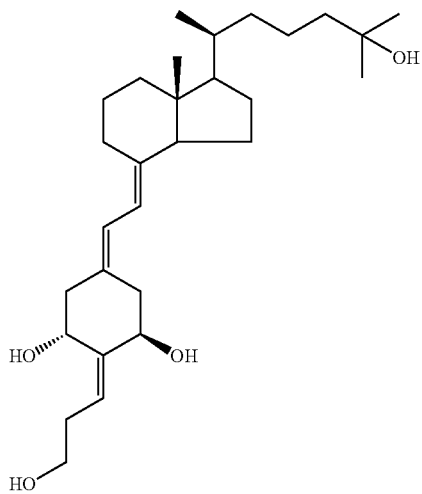

Structurally, the Z-isomer of this (20R) analog is characterized by the general formula Ib shown below and is referred to herein as "2AGR":

Structurally, the Z-isomer of this (20S) analog is characterized by the general formula Id shown below and is referred to herein as "2AGS":

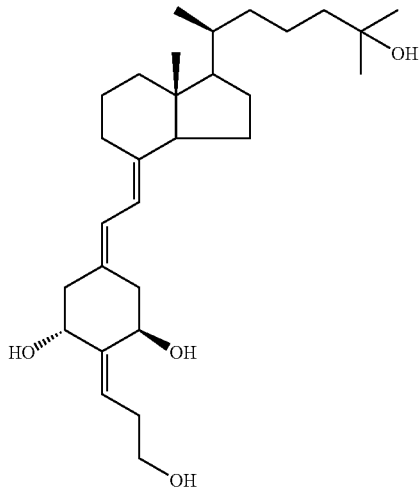

Id

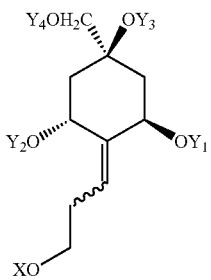

V

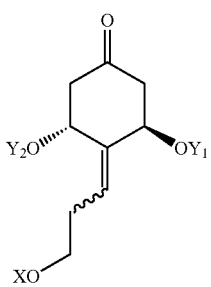

VI

Another 2-propylidene compound that has been synthesized is 2-[(3'-methoxymethoxy)propylidene]-19-nor-1α,25-dihydroxyvitamin D$_3$, and its binding, transcriptional, calcemic (both intestinal calcium transport, and bone calcium mobilization) and differentiation activities were determined. Structurally, this analog is characterized by the general formula Ie shown below, and is referred to herein as "F-Wit";

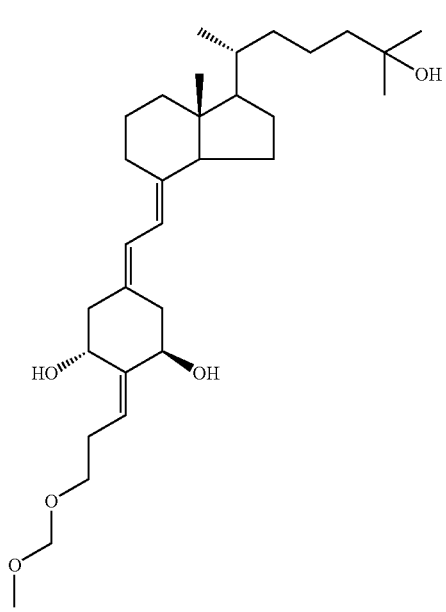

Ie

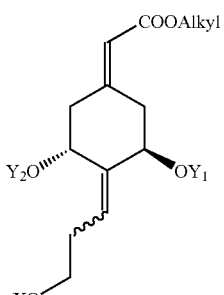

VII

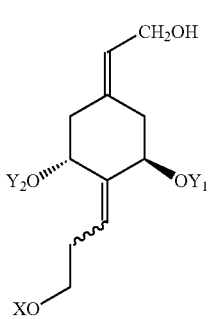

VIII

The invention also provides a novel synthesis for the production of the end products of formula I, and specifically of formulae Ia through Id. In addition, this invention provides novel intermediate compounds formed during the synthesis of the end products. Structurally, these novel intermediates are characterized by the general formulae V, VI, VII, VIII, IX and X below where Y$_1$, Y$_2$, Y$_3$, and Y$_4$, which may be the same or different, are each selected from the group consisting of hydrogen and a hydroxy-protecting group, and X may be an alkyl, hydrogen, hydroxy-protecting group, hydroxyalkyl, alkoxyalkyl and aryloxyalkyl.

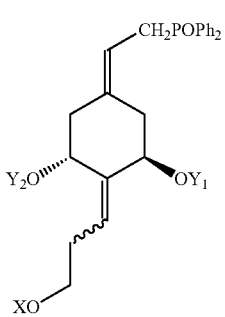

IX

-continued

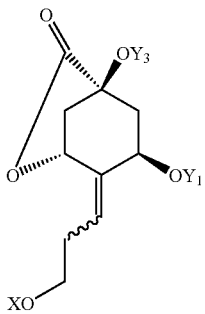

X

DETAILED DESCRIPTION OF THE INVENTION

Figure 1:
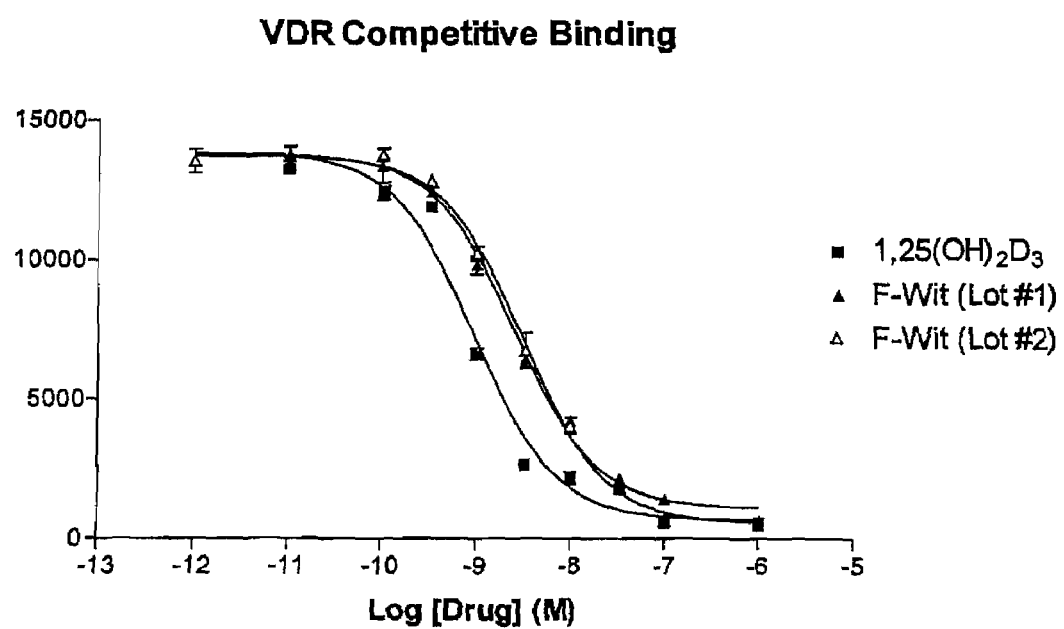
FIG. 1 is a graph illustrating the relative activity of 1α,25-dihydroxyvitamin $D_3$ as well as the herein described and claimed 2-[(3'-methoxymethoxy)propylidene]-19-nor-1α,25-$(OH)_2D_3$ (F-Wit) in binding to the 1α,25-dihydroxyvitamin D pig intestinal nuclear receptor.

As used in the description and in the claims, the term "hydroxy-protecting group" signifies any group commonly used for the temporary protection of hydroxy functions, such as for example, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groupings such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. The word "alkyl" as used in the description or the claims, denotes a straight-chain or branched alkyl radical of 1 to 10 carbons, in all its isomeric forms. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group.

A "protected hydroxy" group is a hydroxy group derivatised or protected by any of the above groups commonly used for the temporary or permanent protection of hydroxy functions, e.g. the silyl, alkoxyalkyl, acyl or alkoxycarbonyl groups, as previously defined. The terms "hydroxyalkyl", "deuteroalkyl" and "fluoroalkyl" refer to an alkyl radical substituted by one or more hydroxy, deuterium or fluoro groups respectively.

It should be noted in this description that the term "24-homo" refers to the addition of one methylene group and the term "24-dihomo" refers to the addition of two methylene groups at the carbon 24 position in the side chain. Likewise, the term "trihomo" refers to the addition of three methylene groups. Also, the term "26,27-dimethyl" refers to the addition of a methyl group at the carbon 26 and 27 positions so that for example $R^3$ and $R^4$ are ethyl groups. Likewise, the term "26, 27-diethyl" refers to the addition of an ethyl group at the 26 and 27 positions so that $R^3$ and $R^4$ are propyl groups.

In the following lists of side chain unsaturated and side chain saturated compounds, if the methyl group attached at the carbon 20 position is in its epi or unnatural configuration, the term "20(S)" or "20-epi" should be included in each of the following named compounds. Also, if the side chain contains an oxygen atom substituted at any of positions 20, 22 or 23, the term "20-oxa," "22-oxa" or "23-oxa," respectively, should be added to the named compound. The named compounds could also be of the vitamin $D_2$ type if desired.

Specific and preferred examples of the 2-propylidene-19-nor-vitamin D compounds of structure I when the side chain is unsaturated are:

2-(3'-hydroxypropylidene)-19-nor-1α-hydroxy-22-dehydrovitamin $D_3$;
2-(3'-hydroxypropylidene)-19-nor-25-hydroxy-22-dehydrovitamin $D_3$;
2-(3'-hydroxypropylidene)-19-nor-1α,25-dihydroxy-22-dehydrovitamin $D_3$;

2-(3'-hydroxypropylidene)-19-nor-24-homo-1,25-dihydroxy-22-dehydrovitamin D$_3$;
2-(3'-hydroxypropylidene)-19-nor-24-dihomo-1,25-dihydroxy-22-dehydrovitamin D$_3$;
2-(3'-hydroxypropylidene) 19-nor-24-trihomo-1,25-dihydroxy-22-dehydrovitamin D$_3$;
2-(3'-hydroxypropylidene)-19-nor-26,27-dimethyl-24-homo-1,25-dihydroxy-22-dehydrovitamin D$_3$;
2-(3'-hydroxypropylidene)-19-nor-26,27-dimethyl-24-dihomo-1,25-dihydroxy-22-dehydrovitamin D$_3$;
2-(3'-hydroxypropylidene)-19-nor-26,27-dimethyl-24-trihomo-1,25-dihydroxy-22-dehydrovitamin D$_3$;
2-(3'-hydroxypropylidene)-19-nor-26,27-diethyl-24-homo-1,25-dihydroxy-22-dehydrovitamin D$_3$;
2-(3'-hydroxypropylidene)-19-nor-26,27-diethyl-24-dihomo-1,25-dihydroxy-22-dehydrovitamin D$_3$;
2-(3'-hydroxypropylidene)-19-nor-26,27-diethyl-24-trihomo-1,25-dihydroxy-22-dehydrovitamin D$_3$;
2-(3'-hydroxypropylidene)-19-nor-26,27-dipropyl-24-homo-1,25-dihydroxy-22-dehydrovitamin D$_3$;
2-(3'-hydroxypropylidene)-19-nor-26,27-dipropyl-24-dihomo-1,25-dihydroxy-22-dehydrovitamin D$_3$; and
2-(3'-hydroxypropylidene)-19-nor-26,27-dipropyl-24-trihomo-1,25-dihydroxy-22-dehydrovitamin D$_3$.

With respect to the above unsaturated compounds, it should be noted that the double bond located between the 22 and 23 carbon atoms in the side chain may be in either the (E) or (Z) configuration. Accordingly, depending upon the configuration, the term "22,23(E)" or "22,23(Z)" could be included in each of the above named compounds. Also, it is common to designate the double bond located between the 22 and 23 carbon atoms with the designation "$\Delta^{22}$". Thus, for example, the fourth named compound above could also be written as 2-(3'-hydroxypropylidene)-19-nor-24-homo-22,23(E)-$\Delta^{22}$-1,25-(OH)$_2$D$_3$ where the double bond is the (E) configuration. Similarly, if the methyl group attached at carbon 20 is in the unnatural configuration, this compound could be written as 2-(3'-hydroxypropylidene)-19-nor-20(S)-24-homo-22,23(E)-$\Delta^{22}$-1,25-(OH)$_2$D$_3$.

Specific and preferred examples of the 2-propylidene-19-nor-vitamin D compounds of structure I when the side chain is saturated are:
2-(3'-hydroxypropylidene)-19-nor-1α-hydroxyvitamin D$_3$;
2-(3'-hydroxypropylidene)-19-nor-25-hydroxyvitamin D$_3$;
2-(3'-hydroxypropylidene)-19-nor-1α,25-dihydroxyvitamin D$_3$;
2-(3'-hydroxypropylidene)-19-nor-24-homo-1,25-dihydroxyvitamin D$_3$;
2-(3'-hydroxypropylidene)-19-nor-24-dihomo-1,25-dihydroxyvitamin D$_3$;
2-(3'-hydroxypropylidene)-19-nor-24-trihomo-1,25-dihydroxyvitamin D$_3$;
2-(3'-hydroxypropylidene)-19-nor-26,27-dimethyl-24-homo-1,25-dihydroxyvitamin D$_3$;
2-(3'-hydroxypropylidene)-19-nor-26,27-dimethyl-24-dihomo-1,25-dihydroxyvitamin D$_3$;
2-(3'-hydroxypropylidene)-19-nor-26,27-dimethyl-24-trihomo-1,25-dihydroxyvitamin D$_3$;
2-(3'-hydroxypropylidene)-19-nor-26,27-diethyl-24-homo-1,25-dihydroxyvitamin D$_3$;
2-(3'-hydroxypropylidene)-19-nor-26,27-diethyl-24-dihomo-1,25-dihydroxyvitamin D$_3$;
2-(3'-hydroxypropylidene)-19-nor-26,27-diethyl-24-trihomo-1,25-dihydroxyvitamin D$_3$;
2-(3'-hydroxypropylidene)-19-nor-26,27-dipropyl-24-homo-1,25-dihydroxyvitamin D$_3$;
2-(3'-hydroxypropylidene)-19-nor-26,27-dipropyl-24-dihomo-1,25-dihydroxyvitamin D$_3$;
2-(3'-hydroxypropylidene)-19-nor-26,27-dipropyl-24-trihomo1,25-dihydroxyvitamin D$_3$;

The preparation of 1α-hydroxy-19-nor-vitamin D compounds, with the substituted propylidene moiety at C-2, of the basic structure I can be accomplished by a common general method, i.e. the condensation of a bicyclic Windaus-Grundmann type ketone II with the allylic phosphine oxide III to the corresponding hydroxy-protected vitamin D analog IV followed by deprotection at C-1 and C-3.

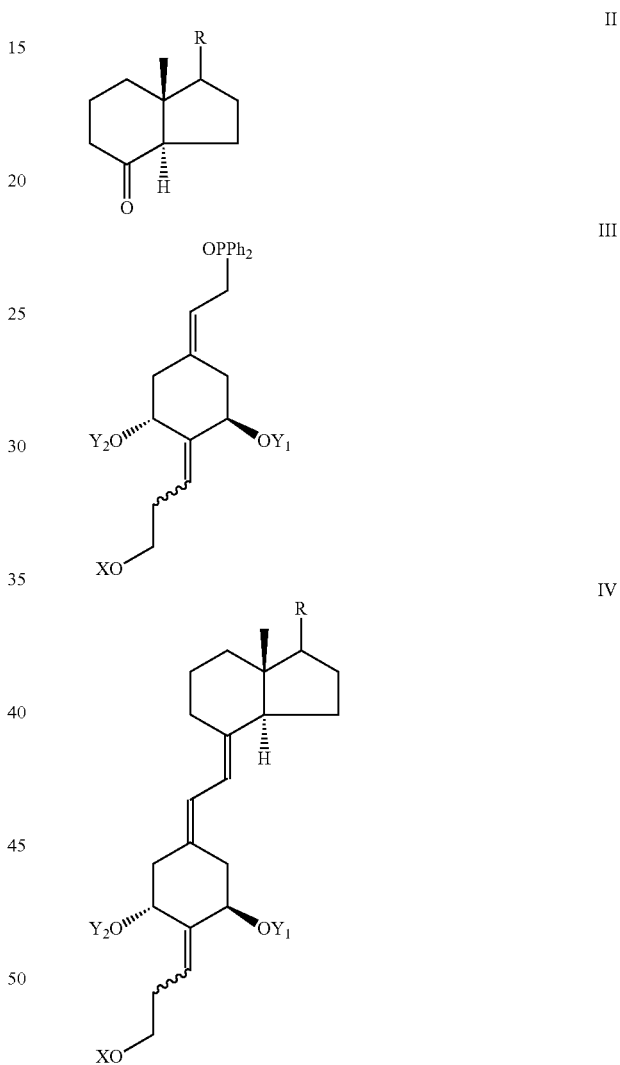

In the structures II and III, groups Y$_1$, Y$_2$, X and R represent groups defined above; Y$_1$, Y$_2$, and X preferably hydroxy-protecting groups, it being also understood that any functionalities in R that might be sensitive, or that interfere with the condensation reaction, be suitable protected as is well-known in the art. The process shown above represents an application of the convergent synthesis concept, which has been applied effectively for the preparation of vitamin D compounds (e.g. Lythgoe et al., J. Chem. Soc. Perkin Trans. I, 590 (1978); Lythgoe, Chem. Soc. Rev. 9, 449 (1983); Toh et al., J. Org. Chem. 48, 1414 (1983); Baggiolini et al., J. Org. Chem. 51, 3098 (1986); Sardina et al., J. Org. Chem. 51, 1264 (1986); J.

Org. Chem. 51, 1269 (1986); DeLuca et al., U.S. Pat. No. 5,086,191; DeLuca et al., U.S. Pat. No. 5,536,713).

Hydrindanones of the general structure II are known, or can be prepared by known methods. Specific important examples of such known bicyclic ketones are the structures with the side chains (a), (b), (c) and (d) described above, i.e. 25-hydroxy Grundmann's ketone (e) [Baggiolini et al., J. Org. Chem., 51, 3098 (1986)]; Grundmann's ketone (f) [Inhoffen et al., Chem. Ber. 90, 664 (1957)]; 25-hydroxy Windaus ketone (g) [Baggiolini et al., J. Org. Chem., 51, 3098 (1986)] and Windaus ketone (h) [Windaus et al., Ann., 524, 297 (1936)]:

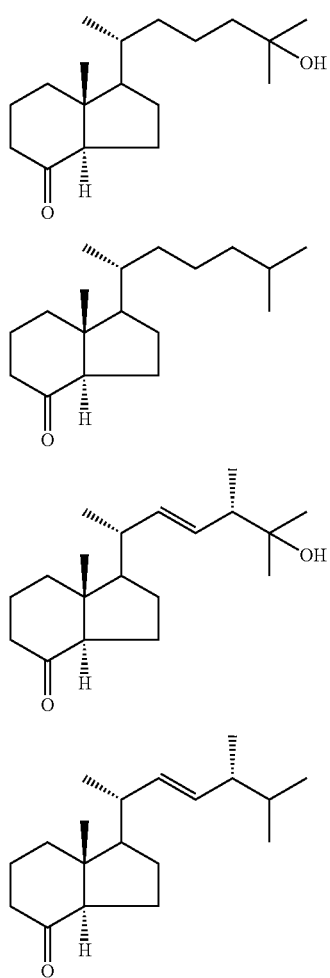

For the preparation of the required phosphine oxides of general structure III, a new synthetic route has been developed starting from bicyclic lactone 1 that was obtained from commercial (1R,3R,4S,5R)-(−)-quinic acid as described previously [Hanessian et al., J. Org. Chem. 62, 465 (1997)]. The overall process of transformation of the starting lactone 1 into the desired A-ring synthons, is summarized by the SCHEME I. Thus, one of the two secondary hydroxy groups of 1 (equatorial hydroxyl at C-3) was selectively protected as t-butyldimethylsilyl ether (TBDMS) and the other was then oxidized with Dess-Martin periodinane reagent to the 4-ketone 3. The tertiary 1-hydroxyl was acetylated and the resulted acetoxy ketone 4 subjected to the Wittig reaction with an ylide generated from the appropriate phosphonium salt. The choice of the phosphonium salt used for this purpose should be made considering the structure of the final 19-norvitamin D. In the case of the attempted synthesis of the 19-norvitamin D analog with the 2-propylidene moiety substituted at the terminal carbon with some functional group other than hydroxyl it might be desirable to use introduce such propylidene fragment to the carbon 4 of the keto compound 4. Such situation is exemplified in the experimental part as EXAMPLE I where the synthesis of 1α,25-dihydroxy-2-[3'-(methoxymethoxy)-propylidene]-19-norvitamin $D_3$ (21) is described. In the case of attempted preparation 1α,25-dihydroxy-2-(3'-hydroxypropylidene)-19-norvitamin D analogs it might be desirable to attach protected 3-hydroxypropylidene fragment to C-4 in the compound 4. Such situation is exemplified in the experimental part as EXAMPLE II where the synthesis of both E- and Z-geometrical isomers of 1α,25-dihydroxy-2-(3'-hydroxypropylidene)-19-norvitamin $D_3$ (24a,b) and their 20S-counterparts (25a,b) is described. The phosphonium salts A and B, used in these processes, were prepared from 3-bromo-1-propanol. Thus, in the first synthesis the Wittig reaction of the keto lactone 4 with ylide generated from phosphonium bromide A and n-butyllithium afforded two isomeric olefinic compounds 5a and 5b in the ratio of ca. 5:1. Simultaneous reduction of the lactone ring and acetate group in the major compound 5a with sodium borohydride or other suitable reducing agent (e.g. lithium aluminum hydride) provided the triol 7 (SCHEME II) which was subsequently oxidized by sodium periodate to the cyclohexanone derivative 9. The next steps of the process comprise protection of the secondary hydroxyl as TBDMS ether and subsequent Peterson reaction of the ketone 11 with methyl(trimethylsilyl)acetate. The resulting mixture of the allylic esters 13a and 13b (ratio of isomers ca. 7:1) was treated with DIBALH or other suitable reducing agent (e.g. lithium aluminum hydride) and the formed allylic alcohols 15a and 15b were then transformed to the desired A-ring phosphine oxides 17a and 17b. This last transformation involved 3 steps, namely, in situ tosylation with n-butyllithium and p-toluenesulfonyl chloride, followed by reaction with diphenylphosphine lithium salt and oxidation with hydrogen peroxide. Alternatively, in the second synthesis the Wittig reaction of the keto lactone 4 was performed with ylide generated from phosphonium bromide B and it afforded two isomeric olefins 6a and 6b in the ratio of ca. 3:2. Reduction and periodate oxidation followed by silylation provided the corresponding keto compound 12. Subsequent Peterson reaction gave a mixture of the allylic esters 14a and 14b (ratio of isomers ca. 6:1) which was converted to the respective phosphine oxides 18a and 18b.

Several 2-methylene-19-nor-vitamin D compounds may be synthesized using the A-ring synthons 17a,b and 18a,b and the appropriate Windaus-Grundmann ketones having the desired side chain structure. Thus, for example, Wittig-Horner coupling of the lithium phosphinoxy carbanion generated from 17a and phenyllithium with the protected 25-hydroxy Grundmann's ketone 19a (SCHEME III), prepared according to published procedure [Sicinski et al., J. Med. Chem. 37, 3730 (1994)], gave the expected protected vitamin compound 20. This, after deprotection with tetrabutylammonium fluoride afforded 1α,25-dihydroxy-2-[3'-(methoxymethoxy)-propylidene]-19-norvitamin $D_3$ (21). Alternatively, Wittig-Horner reaction of the anion generated from 18a,b and phenyllithium with the protected 25-hydroxy Grundmann's ketone 19a, provided after hydroxyls deprotection the expected E- and Z-isomers of 1α,25-dihydroxy-2-(3'-hydroxypropylidene)-19-norvitamin $D_3$ (24a,b), whereas coupling of the phosphine oxides 18a,b with the (20S)-Grundmann's ketone derivative 19b and subsequent hydrolysis resulted in formation of the corresponding E- and Z-isomers of (20S)-1α,25-dihydroxy-2-(3'-hydroxypropylidene)-19-nor-vitamin $D_3$ (25a,b).

As noted above, other 19-nor-vitamin D analogs may be synthesized by the method disclosed herein.

This invention is described by the following illustrative examples. In these examples specific products identified by Arabic numerals (e.g. 1, 2, 3, etc) refer to the specific structures so identified in the preceding description and in the SCHEME I, SCHEME II, and SCHEME III.

EXAMPLES

Chemistry. Melting points (uncorrected) were determined on a Thomas-Hoover capillary melting-point apparatus. Ultraviolet (TV) absorption spectra were recorded with a Perkin-Elmer Lambda 3B UV-VIS spectrophotometer in ethanol. $^1$H nuclear magnetic resonance (NMR) spectra were recorded at 400 and 500 MHz with a Bruker Instruments DMX-400 and DMX-500 Avance console spectrometers in deteriochloroform. $^{13}$C nuclear magnetic resonance (NMR) spectra were recorded at 125 MHz with a Bruker Instruments DMX-500 Avance console spectrometer in deuteriochloroform. Chemical shifts (δ) are reported downfield from internal Me$_4$Si (δ 0.00). Electron impact (EI) mass spectra were obtained with a Micromass AutoSpec (Beverly, Mass.) instrument. High-performance liquid chromatography (HPLC) was performed on a Waters Associates liquid chromatograph equipped with a Model 6000A solvent delivery system, a Model U6K Universal injector, and a Model 486 tunable absorbance detector. THF was freshly distilled before use from sodium benzophenone ketyl under argon.

Example I

Preparation of 1α,25-dihydroxy-2-[3'-(methoxymethoxy)propylidene]-19-norvitamin $D_3$ Referring first to SCHEME I the starting bicyclic lactone 1 was obtained from commercial (−)-quinic acid as described previously [Hanessian et al., J. Org. Chem. 62, 465 (1997)].

(a) Protection of 3-Hydroxy Group in the Lactone 1. (1R, 3R,4S,5R)-1,4-Dihydroxy-3-[(tert-butyldimethylsilyl)oxy]-6-oxa-bicyclo[3.2.1]octan-7-one (2). To a stirred solution of lactone 1 (1.80 g, 10.34 mmol) and imidazole (2.63 g, 38.2 mmol) in anhydrous DMF (14 mL) was added t-butyldimethylsilyl chloride (1.80 g, 11.9 mmol) at 0° C. The mixture was stirred at 0° C. for 30 min and 1 h at room temperature, poured into water and extracted with ethyl acetate and ether. The organic layer was washed several times with water, dried (MgSO$_4$), and evaporated to give a colorless crystalline residue which was crystallized from hexane/ethyl acetate to give 2.12 g of pure 2. The mother liquors were evaporated and purified by flash chromatography. Elution with hexane/ethyl acetate (8:2) gave additional quantity of crystalline monoether 2 (0.14 g, overall yield 76%) and some quantity of crystalline isomeric (3-OH, 4-OTBDMS) ether (0.10 g, 3%). 2: m.p. 90-94° C. (from hexane); $[\alpha]^{24}_D$ −44° (c 1.00 CHCl$_3$); $^1$H NMR (500 MHz, CDCl$_3$) δ 0.095 (6H, s, 2×SiCH$_3$), 0.901 (9H, s, Si-t-Bu), ca. 2.0 (2H, br m, 2α- and 2β-H, 2.29 (1H, ddd, J=11.6, 6.0, 2.6 Hz, 8β-H), 2.63 (1H, d, J=11.6 Hz, 8αH), 3.89 (1H, ddd, J=10.4, 7.0, 4.5 Hz, 3 β-H), 3.98 (1H, t, J=4.6 Hz, 4β-H), 4.88 (1H, dd, J=6.0, 4.8 Hz, 5α-H); $^{13}$C NMR (125 MHz) δ −5.0 (Si—CH$_3$), −4.7 (Si—CH$_3$), 17.9 [C(CH$_3$)$_3$], 25.6 [C(CH$_3$)$_3$], 36.4 (C$_8$), 40.2 (C$_2$), 65.8 (C$_4$), 67.0 (C$_3$), 71.9 (C$_1$), 76.3 (C$_5$), 177.9 (C=O), MS (EI) m/z (relative intensity) 288(M$^+$, 1), 231 (41), 213 (21), 185 (85), 75 (100); HRMS (ESI), exact mass calcd for C$_{13}$H$_{24}$O$_5$SiNa (M$^+$+Na) 311.1291, measured 311.1287; Anal. Calcd for C$_{13}$H$_{24}$O$_5$Si: C, 54.14, H, 8.39. Found: C, 53.94, H, 8.36.

(b) Oxidation of 4-Hydroxy Group in the Dihydroxy Lactone 2.

(1R,3R,5R)-3-[(tert-Butyldimethylsilyl)oxy]-1-hydroxy-6-oxa-bicyclo[3.2.1]octane-4,7-dione (3). To a stirred suspension of Dess-Martin periodinane reagent (6.60 g, 15.5 mmol) in anhydrous CH$_2$Cl$_2$ (100 mL) was added compound 2 (3.86 g, 13.4 mmol). The mixture was stirred at room temperature for 18 h, poured into water and extracted with ethyl acetate. The organic layer was washed several times with water, dried (MgSO$_4$), and evaporated to give an oily residue which slowly crystallized on cooling (3.67 g, 95%). TLC indicated high purity of the obtained ketone 3 which could be used in the next step without further purification. Analytical sample was obtained by recrystallization from hexane. 3: m.p. 92-95° C.; $^1$H NMR (400 MHz, CDCl$_3$) δ 0.040 and 0.133 (3H and 3H, each s, 2×SiCH$_3$), 0.895 (9H, s, Si-t-Bu), 2.15 (1H, dd, J=12.4, 10,4 Hz, 2α-H ), 2.42 (1H, d, J=12.5 Hz, 8α-H), 2.54 (1H, ddd, J=12.4, 9.0, 3.9 Hz, 2β-H), 2.86 (1H, ddd, J=12.5, 6.7, 3.9 Hz, 8β-H), 4.54 (1H, dd, J=10.4, 9.0 Hz, 3β-H), 4.73 (1H, d, J=6.7 Hz, 5α-H); $^{13}$C NMR (125 MHz) δ −5.6 (Si—CH$_3$), −4.8 (Si—CH$_3$), 18.2 [C(CH$_3$)$_3$], 25.6 [C(CH$_3$)$_3$], 42.3 (C$_8$), 43.0 (C$_2$), 70.3 (C$_3$), 71.8 (C$_1$), 78.7 (C$_5$), 177.1 (C=O), 202.4 (C$_4$); MS (EI) m/z (relative intensity) no M$^+$, 271 (M$^+$−CH$_3$, 4), 229 (92), 201 (28), 157 (100); HRMS (ESI) exact mass calcd for C$_9$H$_{13}$O$_5$Si (M$^+$−t-Bu) 229.0532, measured 229.0539; Anal. Calcd for C$_{13}$H$_{22}$O$_5$Si×H$_2$O: C, 51.29, H, 7.95. Found: C, 51.09, H, 7.90.

(c) Acetylation of 1-Hydroxy Group in the Hydroxy Ketone 3.

(1R,3R,5R)-1-Acetoxy-3-[(tert-butyldimethylsilyl)oxy]-6-oxa-bicyclo[3.2.1]octane-4,7-dione (4). Solution of hydroxy ketone 3 (1.64 g, 5.8 mmol) in anhydrous pyridine (12 mL) and acetic anhydride (5.5 mL) was stirred for 3 h at room temperature. It was poured into water and extracted with ethyl acetate. The organic layer was washed with saturated NaHCO$_3$, saturated CuSO$_4$ and water, dried (MgSO$_4$), and evaporated to give an oily residue which was dissolved in hexane/ethyl acetate (8:2) and filtered through short path of silica gel. Evaporation of solvents gave pure crystalline acetate 4 (1.51 g, 81%). Analytical sample was obtained by recrystallization from hexane/ethyl acetate. 4: m.p. 134-7° C.; $[\alpha]^{24}_D$−78° (c 1.00 CHCl$_3$); $^1$H NMR (400 MHz, CDCl$_3$) δ 0.046 and 0.141 (3H and 3H, each s, 2×SiCH$_3$), 0.901 (9H, s, Si-t-Bu), 2.17 (3H, s, CH$_3$CO), 2.28 (1H, dd, J=12.2, 10.4 Hz, 2α-H), 2.32 (1H, d, J=12.1 Hz, 8α-H), 2.65 (1H, ddd, J=12.2, 8.8, 3.9 Hz, 2β-H), 3.56 (1H, ddd, J=12.1, 6.9, 3.9 Hz, 8β-H), 4.58 (1H, dd, J=10.4, 8.8 Hz, 3β-H), 4.80 (1H, d, J=6.9 Hz, 5α-H); $^{13}$C NMR (125 MHz) δ −5.8 (Si—CH$_3$), −4.9 (Si—CH$_3$), 18.2 [C(CH$_3$)$_3$], 20.9 (CH$_3$—C=O), 25.6 [C(CH$_3$)$_3$], 38.3 (C$_8$), 40.3 (C$_2$), 70.4 (C$_3$), 75.3 (C$_1$), 78.4 (C$_5$), 169.1 (CH$_3$—C=O), 171.5 (C=O), 201.8 (C$_4$); MS (EI) m/z (relative intensity) 328 (M$^+$, 6), 271 (100), 256 (38), 229 (54), 211 (53); HRMS (ESI) exact mass calcd for C$_{11}$H$_{15}$O$_6$Si (M$^+$−t-Bu) 271.0638, measured 271.0646; Anal. Calcd for C$_{15}$H$_{24}$O$_6$Si: C, 54.86, H, 7.37. Found: C, 54.88, H, 7.37.

(d) Preparation of the Phosphonium Bromide A.

[3-(Methoxymethoxy)propyl]triphenylphosphonium bromide (A). To a solution of bromomethyl methyl ether (1.3 mL, 16 mmol) and N,N-diisopropylethylamine (4.5 mL, 27.7 mmol) in anhydrous CH$_2$Cl$_2$ (50 mL) at 0° C. was added 3-bromo-1-propanol (1.0 mL, 11 mmol) and the mixture was stirred at 0° C. for 1 h and at room temperature for 20 h. The reaction mixture was poured into 1 N HCl (150 mL), organic phase was separated and water phase was extracted with $CH_2Cl_2$. The combined organic phases were washed with water and diluted $NaHCO_3$, dried ($MgSO_4$), and evaporated to give a yellowish oil. The residue was purified by flash chromatography. Elution with hexane/ethyl acetate (95:5) afforded pure oily 1-bromo-3-(methoxymethoxy)propane (1.12 g, 55%): $^1H$ NMR (400 MHz, $CDCl_3$) δ 2.13 (2H, m, $CH_2$—$C\underline{H}_2$—$CH_2$), 3.37 (3H, s, O—$CH_3$), 3.53 (2H, br t, J=6.5 Hz, Br—$CH_2$), 3.67 (2H, br t, J=5.8 Hz, $CH_2$—$C\underline{H}_2$—O), 4.63 (2H, s, O—$CH_2$—O).

To a solution of 1-bromo-3-(methoxymethoxy)propane (0.46 g, 2.5 mmol) in anhydrous toluene (1.5 mL) was added triphenylphoshine (0.71 g, 2.7 mmol) under argon with stirring. The mixture was heated at 100° C. for 20 h and cooled to room temperature. The liquid was decanted and the solid residue was grounded with spatula, filtered and washed several times with ether. After drying overnight in vacuum dessicator colorless crystals of phosphonium salt A (0.98 g, 88%) could be used in the Wittig reaction without further purification. A: $^1H$ NMR (500 MHz, $CDCl_3$) δ 1.96 (2H, m, $CH_2$—$C\underline{H}_2$—$CH_2$), 3.31 (3H, s, O—$CH_3$), 3.85 (2H, br t, J=5.6 Hz, $CH_2$—$C\underline{H}_2$—O), 4.00 (2H, m, P—$CH_2$), 4.60 (2H, s, O—$CH_2$—O), 7.70, 7.79 and 7.86 (6H, 3H and 6H, each m, Ar—H); Anal. Calcd for $C_{23}H_{26}O_2PBr$: C, 62.03, H, 5.88, Br, 17.94. Found: C, 61.87, H, 5.77, Br, 17.89.

(e) Wittig Reaction of the 4-Ketone 4 with the ylide generated from A.

[(E)- and (Z)-(1R,3R,5R)-1-Acetoxy-3-[(tert-butyldimethylsilyl)oxy]-6-oxa-4-[3'-(methoxymethoxy)propylidene]bicyclo[3.2.1]octan-7-one (5a and 5b). To the phoshonium bromide A (420 mg, 0.94 mmol) in anhydrous THF (5 mL) at 0° C. was added dropwise n-BuLi (1.6 M in hexanes, 1.12 mL, 1.8 mmol) under argon with stirring. After 5 min another portion of A was added (420 mg, 0.94 mmol) and the solution was stirred at 0° C. for 10 min and then at room temperature for 20 min. The orange-red mixture was cooled to −78° C. and siphoned in 2 equal portions (30 min interval) to a solution of keto lactone 4 (300 mg, 0.91 mmol) in anhydrous THF (8 mL). The reaction mixture was stirred at −78° C. and stopped by addition of brine cont. 1% HCl (3 h after addition of the first portion of the Wittig reagent). Ethyl acetate (9 mL), benzene (6 mL), ether (3 mL), sat. $NaHCO_3$ (3 mL), and water (3 ml) were added and the mixture was vigorously stirred at room temperature for 18 h. Then an organic phase was separated, washed with brine, dried ($MgSO_4$), and evaporated. The oily residue (consisting mainly with isomeric 5a and 5b in the ratio of ca. 5:1) was separated by flash chromatography on silica. Elution with hexane/ethyl acetate (85:15) resulted in partial separation of products: 29 mg of 5b, mixture of 5a and 5b (85 mg) and pure 5a (176 mg; total yield 77%). Rechromatography of the mixed fractions resulted in almost complete separation of the products. 5a: $[\alpha]^{24}_D$ −63° (c 0.60 $CHCl_3$);

$^1H$ NMR (500 MHz, $CDCl_3$) δ 0.074 (6H, s, 2×$SiCH_3$), 0.914 (9H, s, Si-t-Bu), 2.13 (3H, s, $OCH_3$), 2.00 (1H, br t, J=11.2, Hz, 2α-H), 2.10 (1H, d, J=10.8 Hz, 8α-H), 2.34 (1H, ddd, J=11.7, 7.0, 2.9 Hz, 2β-H), 2.38 and 2.43 (1H and 1H, each m, =C—$CH_2$), 3.31 (1H, ddd, J=10.8, 6.5, 2.9 Hz, 8β-H), 3.35 (3H, s, O—$CH_3$), 3.54 and 3.60 (1H and 1H, each m, $CH_2$—$C\underline{H}$—O), 4.41 (1H, t, J=8.2 Hz, 3β-H), 4.60 (2H, s, O—$CH_2$—O), 5.52 (1H, d, J=6.5 Hz, 5α-H), 5.71 (1H, br t, J=7.1 Hz, =CH); $^{13}C$ NMR (125 MHz) δ −5.1 (Si—$CH_3$), −4.9 (Si—$CH_3$), 18.1 [$\underline{C}(CH_3)_3$], 21.1 $\underline{C}H_3$—C=O), 25.7 [C($\underline{C}H_3)_3$], 27.5 ($CH_2$—$\underline{C}H_2$—C=), 40.5 ($C_8$), 41.5 ($C_2$), 55.2 (O—$CH_3$), 66.7 (O—$\underline{C}H_2$—$CH_2$), 66.8 ($C_3$), 77.1 ($C_1$), 73.9 ($C_5$), 96.3 (O—$CH_2$—O), 121.9 (=$\underline{C}$—$CH_2$), 136.8 ($C_4$), 169.1 ($CH_3$—$\underline{C}$=O), 172.9 (C=O); MS (EI) m/z (relative intensity), no $M^+$, 383 ($M^+$−$OCH_3$, 3), 357 (10), 325 (44), 297 (12), 267 (15), 265 (40), 237 (89), 75 (100); HRMS (ESI) exact mass calcd for $C_{20}H_{34}O_7SiNa$ ($M^+$+Na) 437.1972, measured 437.1975. 5b: $^1H$ NMR (500 MHz, $CDCl_3$) δ 0.108 and 0.125 (3H and 3H, each s, 2×$SiCH_3$), 0.912 (9H, s, Si-t-Bu), 2.13 (3H, s, $OCH_3$), 2.15 (1H, dd, J=12.6, 8.3 Hz, 2α-H), 2.31 (1H, d, J=10.8 Hz, 8α-H), 2.33 (1H, 2β-H overlapped with 8α-H), 2.67 and 2.73 (1H and 1H, each m, =C—$CH_2$), 3.25 (1H, ddd, J=10.8, 6.3, 2.8 Hz, 8β-H), 3.36 (3H, s, O—$CH_3$), 3.55 (2H, m, $CH_2$—$C\underline{H}_2$—O), 4.61 (2H, s, O—$CH_2$—O), 4.71 (1H, br t, J~7 Hz, 3β-H), 4.94 (1H, d, J=6.3 Hz, 5α-H), 5.64 (1H, dt, J=1.7, 7.1 Hz, =CH); $^{13}C$ NMR (125 MHz) δ −4.6 (Si—$CH_3$), −4.5 (Si—$CH_3$), 17.9 [$\underline{C}(CH_3)_3$], 21.1 ($\underline{C}H_3$—C=O), 25.7 [C($\underline{C}H_3)_3$], 27.8 ($CH_2$—$\underline{C}H_2$—C=), 38.9 ($C_8$), 41.2 ($C_2$), 55.3 (O—$CH_3$), 67.1 (O—$\underline{C}H_2$—$CH_2$), 67.2 ($C_3$), 77.1 ($C_1$), 81.8 ($C_5$), 96.4 (O—$CH_2$—O), 128.9 (=$\underline{C}$—$CH_2$), 134.8 ($C_4$), 169.1 ($CH_3$—$\underline{C}$=O), 173.0 (C=O); MS (EI) m/z (relative intensity), no $M^+$, 383 ($M^+$−$OCH_3$, 2), 357 (2), 325 (22), 297 (17), 267 (35), 265 (14), 237 (96), 75 (100); HRMS (ESI) exact mass calcd for $C_{20}H_{34}O_7SiNa$ ($M^+$+Na) 437.1972, measured 437.1974.

(f) Reduction of the Acetoxy Lactone 5a (SCHEME II).

[(E)-(1'R,3'R,5'R)-3-[(tert-Butyldimethylsilyl)oxy]-1',5-dihydroxy-4'-[3"-(methoxymethoxy)propylidene]cyclohexyl]methanol (7). (a) To a stirred solution of compound 5a (165 mg, 0.40 mmol) in anhydrous ethanol (5 mL) at 0° C. was added $NaBH_4$ (151 mg, 4.0 mmol) and the mixture was stirred at 0° C. for 1 h, then for 10 h at 6° C., and for 2 h at room temperature. The saturated $NH_4Cl$ was added and the mixture was poured into brine and extracted several times with ether and methylene chloride. The extracts were washed with brine, combined, dried ($MgSO_4$), and evaporated. The oily residue was purified by flash chromatography. Elution with hexane/ethyl acetate (2:8) gave pure triol 7 as a colorless oil (115 mg, 79%). 7: $[\alpha]^{24}_D$ −59° (c 1.40 $CHCl_3$); $^1H$ NMR (400 MHz, $CDCl_3$) δ 0.087 and 0.110 (3H and 3H, each s, 2×$SiCH_3$), 0.895 (9H, s, Si-t-Bu), 1.66 (1H, dd, J=13.0, 9.1 Hz, 6β-H), 1.69 (1H, dd, J=13.8, 3.1 Hz, 2β-H), 1.84 (1H, s, OH), 1.96 (1H, ddd, J=13.8, 5.0, 1.7 Hz, 2α-H), 2.04 (1H, ddd, J=13.0, 4.6, 1.7 Hz, 6α-H), 2.54 (1H, s, OH), 2.63 (2H, m, =C—$CH_2$), 3.34 (3H, s, O—$CH_3$), 3.39 and 3.50 (1H and 1H, after $D_2O$: each d, J=11.0 Hz, $C\underline{H}_2$—OH), 3.50 (1H, s, O$\underline{H}$), 3.58 (2H, m, $CH_2$—$C\underline{H}_2$—O), 4.19 (1H, s, OH), 4.47 (1H, m, w/2=10 Hz, 3β-H), 4.63 (2H, s, —O—$CH_2$—O), 4.89 (1H, m; after $D_2O$: dd, J=9.1, 4.6 Hz, 5α-H), 5.51 (1H, t, J=8.3 Hz, =CH); $^{13}C$ NMR (125 MHz) δ −5.2 (Si—$CH_3$), −4.7 (Si—$CH_3$), 18.0 [$\underline{C}(CH_3)_3$], 25.7 [C($\underline{C}H_3)_3$], 27.2 ($CH_2$—$\underline{C}H_2$—C=), 41.3 ($C_2$), 44.1 ($C_6$), 55.4 (O—$CH_3$), 66.4 ($C_5$), 66.7 (O—$\underline{C}H_2$—$CH_2$), 70.3 ($CH_2$—OH), 73.7 ($C_1$), 75.9 ($C_3$), 96.4 (O—$CH_2$—O), 122.0 (=$\underline{C}$—$CH_2$), 144.2 ($C_4$); MS (EI) m/z (relative intensity), no $M^+$, 358 ($M^+$−$H_2O$, 2), 327 (3), 297 (3), 239 (17), 75 (100); HRMS (ESI) exact mass calcd for $C_{18}H_{36}O_6SiNa$ ($M^+$+Na) 399.2179, measured 399.2198. (b) To a solution of compound 5a (186 mg, 0.45 mmol) in anhydrous THF (17 mL) at 0° C. was added $LiAlH_4$ (128 mg, 3.42 mmol) and the mixture was stirred at 0° C. for 1 h and for 3 h at room temperature. The mixture was carefully poured to the saturated solution of $Na_2SO_4$ and extracted several times with ethyl acetate and ether. The organic layer was washed with brine, dried ($MgSO_4$), and evaporated. The oily residue was purified by flash chromatography. Elution with hexane/ethyl acetate (2:8) gave pure triol 8 as a colorless oil (100 mg, 59%).

(g) Cleavage of the Vicinal Diol 7.

[(E)-(3R,5R)-3-[(tert-Butyldimethylsilyl)oxy]-5-hydroxy-4-[3'-(methoxymethoxy)propylidene]]cyclohexanone (9). Sodium periodate-saturated water (1.2 mL) was added to a solution of the triol 7 (79 mg, 0.21 mmol) in methanol (5 mL) at 0° C. The solution was stirred at 0° C. for 1 h, poured into brine, and extracted with ethyl acetate and ether. The extract was washed with brine, dried (MgSO$_4$), and evaporated. An oily residue was redissolved in hexane/CH$_2$Cl$_2$ and applied on a Sep-Pak cartridge. Pure hydroxy ketone 9 (64 mg, 88%) was eluted with hexane/ethyl acetate (7:3) as an oil slowly crystallizing in the refrigerator. 9: $[\alpha]^{24}{}_D$+41° (c 1.45 CHCl$_3$); $^1$H NMR (500 MHz, CDCl$_3$) δ 0.048 and 0.076 (3H and 3H, each s, 2×SiCH$_3$), 0.863 (9H, s, Si-t-Bu), 2.34 (1H, m, one of =C—CH$_2$), 2.50 (1H, dd, J=16.0, 6.0 Hz, 2α-H), 2.62 (1H, m, dd, J=16.1, 3.2 Hz, one of 6-H), 2.65 (1H, m, =C—CH$_2$), 2.70 (1H, dd, J=16.0, 3.4 Hz, 2β-H), 2.75 (1H, dd, J=16.1, 3.4 Hz, one of 6-H), 3.33 (3H, s, O—CH$_3$), 3.53 and 3.74 (1H and 1H, each m, CH$_2$—C$\underline{H}_2$—O), 4.62 (3H, br m, 3β-H and O—CH$_2$—O), 4.95 (1H, t, J~3.3 Hz, 5α-H), 5.73 (1H, dd, J=10.2, 6.3 Hz, =CH); $^{13}$C NMR (125 MHz) δ −4.9 (Si—CH$_3$), −4.7 (Si—CH$_3$), 18.0 [$\underline{C}$(CH$_3$)$_3$], 25.6 [C($\underline{C}$H$_3$)$_3$], 28.0 (CH$_2$—$\underline{C}$H$_2$—C=), 45.3 (C$_2$), 48.3 (C$_6$), 55.4 (O—CH$_3$), 63.1 (C$_5$), 65.7 (O—$\underline{C}$H$_2$—CH$_2$), 70.3 (C$_3$), 96.3 (O—CH$_2$—O), 126.7 (=$\underline{C}$—CH$_2$), 142.5 (C$_4$), 208.7 (C$_1$); MS m/z (relative intensity), no M$^+$, 313 (M$^+$−OCH$_3$, 3), 287 (15), 269 (7), 255 (21), 237 (11), 227 (68), 225 (91), 213 (17), 195 (57), 75 (100); HRMS (ESI) exact mass calcd for C$_{13}$H$_{21}$O$_5$Si (M$^+$−t-Bu) 287.1315, measured 287.1312.

(h) Protection of 5-Hydroxy Group in the Hydroxy Ketone 9.

[(3R,5R)-3,5-Bis[(tert-Butyldimethylsilyl)oxy]-4-[3'-(methoxymethoxy)propylidene]cyclohexanone (11). To a solution of hydroxy ketone 9 (40 mg, 117 μmol) in anhydrous CH$_2$Cl$_2$ (0.4 mL) at −50° C. was added 2,6-lutidine (32 μL, 274 μmol) and t-butyldimethylsilyl triflate (56 μL, 240 μmol). The mixture was stirred for 5 min at −50° C., then it was allowed to warm up to −15° C. and stirred at this temperature for additional 30 min. Benzene and water was added and the mixture was poured into water and extracted with benzene. The extract was washed with saturated CuSO$_4$ and water, dried (MgSO$_4$), and evaporated. The oily residue was redissolved in hexane, and purified by flash chromatography on silica. Elution with hexane/ethyl acetate (95:5) gave pure protected ketone 11 as a colorless oil (30 mg, 57%; 66% based on recovered substrate) and unreacted 9 (6 mg). 11: $[\alpha]^{24}{}_D$−26° (c 0.30 CHCl$_3$); $^1$H NMR (400 MHz, CDCl$_3$) δ 0.019 and 0.065 (3H and 3H, each s, 4×SiCH$_3$), 0.838 and 0.912 (9H and 9H, each s, 2×Si-t-Bu), 2.32 (1H, dd, J=14.1, 10.4 Hz, 2α-H), 2.45 (3H, br m, =C—CH$_2$ and 6α-H), 2.53 (1H, ddd, J=14.4, 3.2, 2.1 Hz, 6β-H), 2.75 (1H, ddd, J=14.1, 5.6, 2.1 Hz, 2β-H), 3.36 (3H, s, O—CH$_3$), 3.58 (2H, m, CH$_2$—C$\underline{H}_2$—O), 4.62 (2H, s, O—CH$_2$—O), 4.75 (1H, ddd, J=10.4, 5.6, 1.4 Hz, 3β-H), 5.01 (1H, t, J~3.2 Hz, 5α-H), 5.70 (1H, dt, J=1.7, 7.8 Hz, =CH); $^{13}$C NMR (125 MHz) δ −5.08 (Si—CH$_3$), −5.06 (Si—CH$_3$), −5.05 (Si—CH$_3$), −5.00 (Si—CH$_3$), 17.9 [$\underline{C}$(CH$_3$)$_3$], 25.5 [C($\underline{C}$H$_3$)$_3$], 27.7 (CH$_2$—C$\underline{H}_2$—C=), 50.2 (C$_6$), 52.4 (C$_2$), 55.2 (O—CH$_3$), 65.8 (C$_3$), 67.1 (O—CH$_2$—CH$_2$), 67.8 (C$_5$), 96.4 (O—CH$_2$—O), 118.5 (=$\underline{C}$—CH$_2$), 141.5 (C$_4$), 207.5 (C$_1$); MS (EI) m/z (relative intensity) 443 (M$^+$+H, 2), 427 (M$^+$−CH$_3$, 5), 401 (55), 371 (15), 339 (20), 75 (100); exact mass calcd for C$_{12}$H$_{43}$O$_4$Si$_2$ (M$^+$−CH$_3$) 427.2700, measured 427.2701.

Preparation of the Allylic Esters 13a and 13b.

[(E)- and (Z)-(3'R,5'R)-3',5'-Bis[(tert-butyldimethylsilyl)oxy]-4'-[3''-(methoxymethoxy)propylidene]cyclohexylidene]acetic Acid Methyl Esters (13a and 13b). To a solution of diisopropylamine (25 μL, 0.18 mmol) in anhydrous THF (0.15 mL) was added n-BuLi (2.5 M in hexanes, 72 μL, 0.18 mmol) under argon at −78° C. with stirring, and methyl(trimethylsilyl)acetate (30 μL, 0.18 mmol) was then added. After 15 min, the ketone 11 (38.4 mg, 84 μmol) in anhydrous THF (0.2 mL) was added. The solution was stirred at −78° C. for additional 2 h and the reaction mixture was quenched with wet ether, poured into brine and extracted with ether and benzene. The combined extracts were washed with brine, dried (MgSO$_4$), and evaporated. An oily residue was redissolved in hexane and applied on a Sep-Pak cartridge. Pure allylic esters 13a and 13b (37.2 mg, 86%; isomer ratio of 13a:13b=ca. 7:1) were eluted with hexane/ethyl acetate (97:3). Separation of the products was achieved by HPLC (10 mm×25 cm Zorbax-Sil column, 4 mL/min) using the hexane/ethyl acetate (95:5) solvent system. Pure compounds 13a and 13b were eluted at R$_V$ 41 mL and 44 mL, respectively, as colorless oils.

13a: $^1$H NMR (500 MHz, CDCl$_3$) δ −0.006, 0.056, 0.078, 0.107 (each 3H, each s, 4×SiCH$_3$), 0.832 and 0.923 (9H and 9H, each s, 2×Si-t-Bu), 1.87 (1H, t, J=11.8 Hz, 2α-H), 2.28 (1H, br d, J=13.2 Hz, 6α-H), 2.34 (1H, br d, J=13.2 Hz, 6β-H), 2.42 (2H, q, J~7 Hz, =C—CH$_2$), 3.36 (3H, s, CH$_2$—O—C$\underline{H}_3$), 3.55 (2H, m, CH$_2$—C$\underline{H}_2$—O), 3.70 (3H, s, CO—O—CH$_3$), 4.14 (1H, dd, J=12.8, 3.8 Hz, 2β-H), 4.45 (1H, br m, 3β-H), 4.62 (2H, s, O—CH$_2$—O), 4.88 (1H, narr m, 5α-H), 5.55 (1H, br t, J=7.5 Hz, =C$\underline{H}$—CH$_2$), 5.65 (1H, br s, =CH—CO); MS (EI) m/z (relative intensity) no M$^+$, 499 (M$^+$−CH$_3$, 2), 482 (11), 469 (31), 457 (65), 425 (63), 351 (70), 293 (76), 89 (100); HRMS (ESI) exact mass calcd for C$_{26}$H$_{50}$O$_6$Si$_2$Na 537.3044, measured 537.3018.

13b: $^1$H NMR (500 MHz, CDCl$_3$) δ −0.008, 0.048, 0.057 and 0.063 (each 3H, each s, 4×SiCH$_3$), 0.804 and 0.915 (9H and 9H, each s, 2×Si-t-Bu), 1.95 (1H, br d, J=13.8 Hz, 2β-H), 2.17 (1H, t, J~11.6 Hz, 6β-H), 2.42 (2H, m, =C—CH$_2$), 2.55 (1H, ddd, J~12.4, ~5.0, ~1.2 Hz, 6α-H), 3.36 (3H, s, CH$_2$—O—C$\underline{H}_3$), 3.55 (2H, m, CH$_2$—C$\underline{H}_2$—O), 3.67 (3H, s, CO—O—CH$_3$), 3.96 (1H, br d, J=13.8 Hz, 2α-H), 4.51 (1H, br m, 5α-H), 4.62 (2H, s, O—CH$_2$—O), 4.89 (1H, narr m, 3β-H), 5.50 (1H, br t, J=7.5 Hz, =C$\underline{H}$—CH$_2$), 5.80 (1H, br s, =CH—CO); MS m/z (relative intensity) no M$^+$, 499 (M$^+$−CH$_3$, 4), 482 (14), 469 (34), 457 (82), 425 (69), 351 (58), 293 (59), 89 (100); HRMS (ESI) exact mass calcd for C$_{26}$H$_{50}$O$_6$Si$_2$Na 537.3044, measured 537.3053.

(j) Reduction of the Allylic Esters 13a and 13b.

2-[(E)- and (Z)-(3'R,5'R)-3',5'-Bis[(tert-butyldimethylsilyl)oxy]-4'-[3''-(methoxymethoxy)propylidene]cyclohexylidene]ethanol (15a and 15b). Diisobutylaluminum hydride (1.0 M in toluene, 0.3 5 mL), 0.35 mmol) was slowly added to a stirred solution of the allylic esters 13a and 13b (37.2 mg, 74 μmol) in toluene/methylene chloride (2:1, 1.5 mL) at −78° C. under argon. Stirring was continued at −78° C. for 1 h, the mixture was quenched by addition of potassium sodium tartrate (2 N, 2 mL), aq. HCl (2 N, 2 mL) and H$_2$O (24 mL), and then diluted with ether and benzene. The organic layer was washed with diluted NaHCO$_3$ and brine, dried (MgSO$_4$), and evaporated. The residue was purified by flash chromatography. Elution with hexane/ethyl acetate (95:5) resulted in partial separation of products: 16 mg of 15a, mixture of 15a and 15b (15 mg) and pure 15b (3 mg; total yield 97%). Rechromatography of the mixed fractions resulted in almost complete separation of the products.

15a (major): $^1$H NMR (500 MHz, CDCl$_3$) δ −0.007, 0.057, and 0.067 (3H, 6H and 3H, each s, 4×SiCH$_3$), 0.839 and 0.916 (9H and 9H, each s, 2×Si-t-Bu), 1.81 (1H, t, J=11.7 Hz, 2α-H), 2.17 (1H, d, J=13.4 Hz, 6α-H), 2.26 (1H, br d, J=13.4 Hz, 6β-H), 2.41 (2H, q, J=7 Hz, =C—C$\underline{H}_2$—CH$_2$), 2.86 (1H, dd, J=12.5, 3.8 Hz, 2β-H), 3.36 (3H, s, O—CH$_3$), 3.54 (2H, m, CH$_2$—C$\underline{H}_2$—O), 4.38 (1H, dd, J=10.6, 3.8 Hz, 3β-H), 4.17 (2H, t, J~6 Hz; after D$_2$O: d, J=6.9 Hz, C$\underline{H}_2$—OH), 4.62

(2H, s, O—CH$_2$—O), 4.81 (1H, narr m, 5α-H), 5.48 (2H, m, 2×=C$\underline{H}$); MS (EI) m/z (relative intensity) 486 (M$^+$, 3), 468 (30), 454 (17), 441 (32), 429 (24), 423 (34), 89 (100); HRMS (ESI) exact mass calcd for C$_{25}$H$_{50}$O$_5$Si$_2$Na 509.3095, measured 509.3111.

15b (minor): $^1$H NMR (500 MHz, CDCl$_3$) δ 0.011, 0.054, 0.069 (3H, 3H and 6H, each s, 4×SiCH$_3$), 0.850 and 0.917 (9H and 9H, each s, 2×Si-t-Bu), 1.88 (1H, br d, J=13.4 Hz, 2β-H), 2.03 (1H, t, J=11.4 Hz, 6β-H), 2.42 (2H, m, =C—CH$_2$), 2.51 (1H, ddd, J=12.0, 4.8, 1.2 Hz, 6α-H), 2.75 (1H, br d, J=13.4 Hz, 2α-H), 3.36 (3H, s, O—CH$_3$), 3.55 (2H, m, CH$_2$—C$\underline{H}_2$—O), 4.02 and 4.15 (1H and 1H, each m; after D$_2$O: each dd, J=11.8, 7.2 Hz, C$\underline{H}_2$—OH), 4.40 (1H, br m, 5α-H), 4.62 (2H, s, O—CH$_2$—O), 4.90 (1H, narr m, 3β-H), 5.53 (1H, br t, J=7.4 Hz, =C$\underline{H}$—CH$_2$), 5.71 (1H, t, J=7.2 Hz, =C$\underline{H}$—CH$_2$—OH); MS (EI) m/z (relative intensity) 486 (M$^{30}$, 5), 468 (27), 454 (11), 441 (22), 429 (30), 423 (29), 89 (100); HRMS (ESI) exact mass calc. for C$_{25}$H$_{50}$O$_5$Si$_2$Na 509.3095, measured 509.3108.

(k) Conversion of the Allylic Alcohols 15a and 15b into Phosphine Oxides 17a and 17b.

[2-[(E)- and (Z)-(3'R,5'R)-3',5'-Bis[(tert-butyldimethylsilyl)oxy]-4'-[3"-(methoxymethoxy)propylidene]cyclohexylidene]ethyl]diphenylphosphine Oxides (17a and 17b). To the allylic alcohols 15a and 15b (ca. 7:1, 34 mg, 70 μmol) in anhydrous THF (0.8 mL) was added n-BuLi (2.5 M in hexanes, 28 μL, 70 μmol) under argon at 0° C. with stirring. Freshly recrystallized tosyl chloride (14.0 mg, 73 μmol) was dissolved in anhydrous THF (190 μL) and added to the allylic alcohol-BuLi solution. The mixture was stirred at 0° C. for 5 min and set aside at 0° C. In another dry flask with air replaced by argon, n-BuLi (2.5 M in hexanes, 140 μL, 0.35 mmol) was added to Ph$_2$PH (62 μL, 0.34 mmol) in anhydrous THF (420 μL) at 0° C. with stirring. The red solution was siphoned under argon pressure to the solution of tosylate until the orange color persisted (ca. ¼ of the solution was added). The resulting mixture was stirred an additional 40 min at 0° C., and quenched by addition of H$_2$O (40 μl). Solvents were evaporated under reduced pressure and the residue was redissolved in methylene chloride (1.0 mL) and stirred with 10% H$_2$O$_2$ (0.5 mL) at 0° C. for 1 h. The organic layer was separated, washed with cold aq. sodium sulfite and H$_2$O, dried (MgSO$_4$), and evaporated. The residue was subjected to flash chromatography. Elution with hexane/ethyl acetate (85:15) gave unchanged allylic alcohols (3.9 mg). Subsequent elution with benzene/ethyl acetate (7:3) resulted in partial separation of products: 27.6 mg of 17a, mixture of 17a and 17b (2 mg) and pure 17b (2 mg; total yield 68%). Analytical samples of both isomers were obtained after HPLC (10 mm×25 cm Zorbax-Sil column, 4 mL/min) purification using hexane/2-propanol (9:1) solvent system. Pure oily compounds 17a and 17b were eluted at R$_V$ 41 mL and 44 mL, respectively.

17a: $^1$H NMR (500 MHz, CDCl$_3$) δ -0.031,-0.013, 0.017, and 0.024 (each 3H, each s, 4×SiCH$_3$), 0.795 and 0.899 (9H and 9H, each s, 2×Si-t-Bu), 1.47 (1H, br t, J~11 Hz, 2α-H), 2.06 (1H, br m, 6α-H), 2.23 (1H, d, J=13.5 Hz, 6β-H), 2.37 (2H, q, J=7.0, =C—CH$_2$—CH$_2$), 2.62 (1H, dd, J=12.8, 4.5 Hz, 2β-H), 3.34 (3H, s, O—CH$_3$), 3.51 (2H, m, CH$_2$—C$\underline{H}_2$—O), 4.33 (1H, dd, J=10.6, 4.5 Hz, 3β-H), 3.15 (2H, dd, J=15.2, 7.6 Hz, CH$_2$—PO), 4.60 (2H, s, O—CH$_2$—O), 4.74 (1H, narr m, 5α-H), 5.28 (1H, m, =C$\underline{H}$—CH$_2$—PO), 5.44 (1H, t, J~7 Hz, =C$\underline{H}$—CH$_2$—CH$_2$), 7.45, 7.52 and 7.73 (4H, 2H and 4H, each m, Ar—H); MS (EI) m/z (relative intensity) no M$^+$, 613 (100), 538 (9), 481 (31), 449 (22); HRMS (ESI) exact mass calcd for C$_{37}$H$_{59}$O$_5$Si$_2$PNa 693.3536, measured 693.3506.

17b: $^1$H NMR (500 MHz, CDCl$_3$) δ -0.035, 0.018, 0.022, and 0.030 (each 3H, each s, 4×SiCH$_3$), 0.822 and 0.885 (9H and 9H, each s, 2×Si-t-Bu), 1.47 (1H, br d, J=12.9 Hz, 2β-H), 1.93 (1H, m, 6β-H), 2.36 (2H, q, J=7.2 Hz, =C—CH$_2$), 2.46 (2H, br m, 2α- and 6α-H), 3.03 and 3.17 (1H and 1H, each m, CH$_2$—PO), 3.35 (3H, s, O—CH$_3$), 3.50 (2H, m, CH$_2$—C$\underline{H}_2$—O), 4.36 (1H, dd, J=10.6, 4.0 Hz, 5α-H), 4.60 (2H, s, O—CH$_2$—O), 4.75 (1H, narr m, 3β-H), 5.39 (1H, m, =C$\underline{H}$—CH$_2$—PO), 5.44 (1H,br t, J=7.3 Hz, =C$\underline{H}$—CH$_2$), 7.4-7.75 (10H, br m, Ar—H); MS (EI) m/z (relative intensity) no M$^+$, 613 (100), 538 (28), 481 (90), 449 (80); HRMS (ESI) exact mass calcd for C$_{37}$H$_{59}$O$_5$Si$_2$PNa 693.3536, measured 693.3538.

(l) Wittig-Horner Coupling of the Protected 25-Hydroxy Grundmann's

1α-[(tert-Butyldimethylsilyl)oxy]-2-[3'-(methoxymethoxy)propylidene]-25-[(triethylsilyl)oxy]-19-norvitamin D$_3$ tert-Butyldimethylsilyl Ether (20). To a solution of phosphine oxide 17a (15.5 mg, 23 μmol) in anhydrous THF (0.25 mL) at -78° C. was slowly added phenyllithium (1.8 M in cyclohexane/ether, 13 μL, 23 μmol) under argon with stirring. The solution turned deep orange. The mixture was stirred at -78° C. for 20 min and a precooled (-78° C.) solution of protected hydroxy ketone 19a (19 mg, 48 μmol), prepared according to published procedure [Sicinski et al., J. Med. Chem. 37, 3730 (1994)], in anhydrous THF (0.25 mL) was slowly added. The mixture was stirred under argon at -78° C. for 3 h and at 6° C. for 16 h. Ethyl acetate and water were added, and the organic phase was washed with brine, dried (MgSO$_4$), and evaporated. The residue was dissolved in hexane, applied on a silica Sep-Pak cartridge, and washed with hexane/ethyl acetate (98.2, 10 mL) to give 19-norvitamin derivative 20 (9.5 mg, 48%). The Sep-Pak was then washed with hexane/ethyl acetate (96.4, 10 mL) to recover some unchanged C,D-ring ketone 19a (10 mg), and with ethyl acetate (10 mL) to recover diphenylphosphine oxide 17a (1 mg). 20: UV (in hexane) λ$_{max}$ 244.0, 252.5, 262.5 nm; $^1$H NMR (500 MHz, CDCl$_3$) δ -0.015, 0.056 0.061, and 0.069 (each 3H, each s, 4×SiCH$_3$), 0.556 (3H, s, 18-H$_3$), 0.565 (6H, q, J=7.9 Hz, 3×SiCH$_2$), 0.821 and 0.921 (9H and 9H, each s, 2×Si-t-Bu), 0.930 (3H, d, J~7 Hz, 21-H$_3$), 0.947 (9H, t, J=7.9 Hz, 3×SiCH$_2$C$\underline{H}_3$), 1.191 (6H, s, 26- and 27-H$_3$), 1.79 (1H, t, J=12.2 Hz, 10α-H), 1.90 (1H, m), 2.00 (2H, m), 2.20 (1H, br, d, J=13.2 Hz, 4β-H), 2.29 (1H, br d, J=13.2 Hz, 4α-H),2.41 (2H, q, J~7 Hz, =CH—C$\underline{H}_2$) 2.79 (1H, br d, J=12.6 Hz, 9β-H), 3.04 (1H, dd, J=12.4, 4.5 Hz, 10β-H), 3.36 (3H, s, O—CH$_3$),3.54 (2H, m, CH$_2$—C$\underline{H}_2$—O), 4.35 (1H, m, w/2=21 Hz, 1β-H),4.62 (2H, s, O—CH$_2$—O), 4.81 (1H, t, J~2.7 Hz, 3α-H), 5.47 (1H, dt, J=1.5, 7.6 Hz, $\underline{H}$C=C—CH$_2$), 5.87 and 6.12 (1H and 1H, each d, J=11.0 Hz, 7- and 6-H).

(m) Hydrolysis of the Silyl Protecting Groups in the 19-Norvitamin D$_3$ Derivative 20.

1α,25-Dihydroxy-2-[3'-(methoxymethoxy)propylidene]-19-norvitamin D$_3$ (21). To a solution of the protected 19-norvitamin D$_3$ 20 (3.0 mg, 3.5 μmol) in anhydrous THF (200 μl) was added tetrabutylammonium fluoride (1.0 M in THF, 210 μL, 210 μmol). The mixture was stirred under argon at room temperature for 18 h, poured into brine and extracted with ethyl acetate. Organic extracts were washed with brine, dried (MgSO$_4$), and evaporated. The residue was purified by HPLC (10 mm×25 cm Zorbax-Sil column, 4 mL/min) using hexane/2-propanol (75:25) solvent system. Analytically pure 19-norvitamin 21 (1.27 mg, 71%) was collected at R$_V$ 26 mL. The compound gave also a single peak on reversed-phase HPLC (6.2 mm×25 cm Zorbax-ODS column, 2 mL/min) using methanol/water (8:2) solvent system; it was collected at R$_V$ 35 mL. 21: WV (in EtOH) λ$_{max}$ 243.5, 252.0, 262.0 nm; $^1$H NMR (500 MHz, CDCl$_3$) δ 0.549 (3H, s, 18-H$_3$), 0.940 (3H, d, J=6.4 Hz, 21-H$_3$), 1.220 (6H, s, 26- and 27-H$_3$), 2.38 (1H, m, one of =CH—CH$_2$), 2.47 (2H, narr m, 4α- and 4β-H), 2.59 (1H, m, one of =CH—CH$_2$), 2.82 (1H, br d, J=12.8 Hz, 9β-H), 3.14 (1H, dd, J=13.1, 4.9 Hz, 10β-H), 3.34 (3H, s, O—CH$_3$), 3.55 and 3.63 (1H and 1H, each m, CH$_2$—CH$_2$—O), 4.44 (1H, m, w/2=20 Hz, 1β-H), 4.62 (2H, s, O—CH$_{2—O)}$, 4.84 (1H, m, w/2=10 Hz, 3α-H), 5.68 (1H, t, J=7.4 Hz, HC=C—CH$_2$), 5.88 and 6.31 (1H and 1H, each d, J=11.2 Hz, 7- and 6-H); HRMS (ESI) exact mass calcd for C$_{31}$H$_{52}$O$_5$Na 527.3712, measured 527.3702.

Example II

Preparation of 1α,25-dihydroxy-2-(3'-hydroxypropylidene)-19-norvitamin D$_3$ compounds Referring first to SCHEME I the keto lactone 4 was obtained from commercial (−)-quinic acid as described in the Example I (a-c).

(a) Preparation of the Phosphonium Bromide B.

[3-[(tert-Butyldimethylsilyl)oxy]propyl]triphenylphosphonium bromide (B). To a solution of 1-bromo-3-[(tert-butyldimethylsilyl)oxy]propane (2.18 g, 8.56 mmol) in anhydrous benzene (1.6 mL) was added triphenylphoshine (2.64 g, 10.2 mmol) under argon with stirring. The mixture was heated at 85° C. for 18 h and cooled to room temperature. The liquid was decanted and the solid residue was grounded with spatula, filtered and washed several times with ether. Colorless crystals of phosphonium salt B (3.7 g) were purified by silica column chromatography. Pure salt B (3.04 g, 69%) was eluted with chloroform/methanol (96:4). B: $^1$H NMR (500 MHz, CDCl$_3$) δ 0.039 (6H, s, 2×SiCH$_3$), 0.857 (9H, s, Si-t-Bu), 1.93 (2H, m, CH$_2$—CH$_2$—CH$_2$), 3.86-3.94 (4H, br m, CH$_2$—CH$_2$—O and P—CH$_2$), 7.70, 7.79 and 7.85 (6H, 3H and 6H, each m, Ar—H).

(b) Wittig Reaction of the 4-Ketone 4 with the Ylide Generated from B.

[(E)- and (Z)-(1R,3R,5R)-1-Acetoxy-3-[(tert-butyldimethylsilyl)oxy]-6-oxa-4-[3'-((tert-butyldimethylsilyl)oxy) propylidene]bicyclo[3.2.1]octan-7-one (6a and 6b). To the phoshonium bromide B (1.55 g, 3.04 mmol) in anhydrous THF (42 mL) at −20° C. was added dropwise n-BuLi (2.0 M in cyclohexane, 1.50 mL, 3.00 mmol) under argon with stirring. and the solution was stirred at −20° C. for 15 min. The orange-red mixture was cooled to −45° C. and siphoned during 15 min to a solution of keto acetate 4 (700 mg, 2.13 mmol) in anhydrous THF (24 mL). The reaction mixture was stirred at −40° C. for 2 h and stopped by addition of brine cont. 1% HCl. Ethyl acetate (30 mL), benzene (20 mL), ether (10 mL), saturated NaHCO$_3$ (10mL), and water (10 ml) were added and the mixture was vigorously stirred at room temperature for 18 h. Then an organic phase was separated, washed with brine, dried (MgSO$_4$), and evaporated. The residue (consisting mainly with isomeric 6a and 6b in the ratio of ca. 3:2) was purified by flash chromatography on silica. Elution with hexane/ethyl acetate (9:1) gave the mixture of products 6a and 6b (905 mg, 87%). Analytical samples of both isomers were obtained after HPLC (10 mm×25 cm Zorbax-Sil column, 4 mL/min) separation using hexane/ethyl acetate (9:1) solvent system. Pure oily compounds 6a and 6b were eluted at R$_V$ 28 mL and 29 mL, respectively.

6a: $^1$H NMR (500 MHz, CDCl$_3$) δ 0.049 and 0.073 (6H and 6H, each s, 4×SiCH$_3$), 0.889 and 0.914 (9H and 9H, each s, 2×Si-t-Bu), 2.01 (1H, br t, J=11.0 Hz, 2α-H), 2.07 (1H, d, J=10.5 Hz, 8α-H), 2.13 (3H, s, OAc), 2.26-2.36 (3H, m, 2β-H overlapped with =C—CH$_2$), 3.29 (1H, ddd, J=10.5, 6.4, 2.8 Hz, 8β-H), 3.65 (2 H, m, CH$_2$—CH$_2$—O), 4.40 (1H, ~t, J=8.5 Hz, 3β-H), 5.50 (1H, d, J=6.4 Hz, 5α-H), 5.71 (1H, t, J=7.3 Hz, =CH), MS (EI) m/z (relative intensity) no M$^+$, 469 (M$^+$−Me, 1), 427 (64), 367 (13), 337 (26), 73 (100); HRMS (ESI) exact mass calcd for C$_{24}$H$_{44}$O$_6$Si$_2$Na (M$^+$+Na) 507.2574, measured 507.2575.

6b: $^1$H NMR (500 MHz, CDCl$_3$) δ 0.042 (6H, s, 2×SiCH$_3$), 0.098 and 0.117 (3H and 3H, each s, 2×SiCH$_3$), 0.885 and 0.907 (9H and 9H, each s, 2×Si-t-Bu), 2.13 (3H, s, OAc), 2.14 (1H, m, 2α-H), 2.31 (1H, 2β-H overlapped with 8α-H), 2.32 (1H, d, J=11.0 Hz, 8α-H), 2.51 and 2.64 (1H and 1H, each m, =C—CH$_2$), 3.24 (1H, m, 8β-H), 3.62 (2H, m, CH$_2$—CH$_2$—O), 4.69 (1H, ~t, J=7.2 Hz, 3β-H), 4.93 (1H, d, J=6.3 Hz, 5α-H), 5.63 (1H, t, J=7.0 Hz, =CH), MS (EI) m/z (relative intensity) no M$^+$, 469 (M$^+$−Me, 1), 427 (32), 367 (13), 337 (40), 73 (100); HRMS (ESI) exact mass calcd for C$_{24}$H$_{44}$O$_6$Si$_2$Na (M$^+$+Na) 507.2574, measured 507.2560.

(c) Reduction of the Acetoxy Lactones 6a and 6b (SCHEME II).

[(E)- and (Z)-(1'R,3'R,5'R-3-[(tert-Butyldimethylsilyl) oxy]-1',5-dihydroxy-4'-[3"-[((tert-butyldimethylsilyl)oxy) propylidene]cyclohexyl]methanol (8a and 8b). To a stirred solution of compounds 6a and 6b (150 mg, 0.309 mmol) in anhydrous ethanol (4 mL) at 0° C. was added NaBH$_4$ (116 mg, 3.09 mmol) and the mixture was stirred at room temperature for 21 h. The mixture was poured to the saturated NH$_4$Cl and extracted several times with ethyl acetate. The organic layer was washed with brine, dried (MgSO$_4$), and evaporated. The oily residue was purified by silica chromatography. Elution with hexane/ethyl acetate (4:6) gave a semicrystalline mixture of triols 8a and 8b (136 mg, 98%).

8a (major): [α]$^{24}_D$−53° (c 1.00 CHCl$_3$); $^1$H NMR (500 MHz, CDCl$_3$) δ 0.077, 0.082, 0.084 and 0.110 (4×3H, each s, 4×SiCH$_3$), 0.887 and 0.902 (9H and 9H, 2×s, 2×Si-t-Bu), 1.58 (1H, dd, J=12.8, 10.2 Hz, 6'β-H), 1.62 (1H, dd, J=14.0, 2.8 Hz, 2'β-H), 2.03 (1H, ddd, J=14.0, 3.9, 1.9 Hz, 2'α-H), 2.11 (1H, ddd, J=12.8, 4.5, 1.9 Hz, 6'α-H), 2.46 and 2.66 (1H and 1H, each m, =C—CH$_2$), 3.35 and 3.47 (1H and 1H, after D$_2$O: 2×d, J=10.8 Hz, 1-H$_2$), 3.68 (2H, m, CH$_2$—CH$_2$—O), 4.46 (1H, ~t, J=3.3 Hz, 3'β-H), 4.88 (1H, after D$_2$O: dd, J=10.2, 4.5 Hz, 5'α-H), 5.45 (1H, t, J=8.6 Hz, =CH); $^{13}$C NMR (125 MHz) δ −5.6 (Si—CH$_3$), −5.38 (Si—CH$_3$), −5.36 (Si—CH$_3$), −4.5 (Si—CH$_3$), 17.9 [C(CH$_3$)$_3$], 18.4 [C(CH$_3$)$_3$], 25.7 [C(CH$_3$)$_3$], 26.0 [C(CH$_3$)$_3$], 29.2 (CH$_2$—CH$_2$—C=), 40.4 (C$_{2'}$), 44.1 (C$_{6'}$), 62.2 (O—H$_2$—C$_2$), 66.2 (C$_{5'}$), 70.3 (C$_1$), 73.8 (C$_{1'}$), 74.1 (C$_{3'}$), 121.9 (=C—CH$_2$), 145.0 (C$_{4'}$), HRMS (ESI) exact mass calcd for C$_{22}$H$_{46}$O$_5$Si$_2$Na (M$^+$+Na) 469.2824, measured 469.2781.

(d) Cleavage of the Vicinal Diols 8a and 8b.

[(E)- and (Z)-(3R,5R-3-[(tert-Butyldimethylsilyl)oxy]-5-hydroxy-4-[3'-[((tert-butyldimethylsilyl)oxy)propylidene]] cyclohexanone (10a and 10b). Sodium periodate-saturated water (1.6 mL) was added to a solution of the triols 8a and 8b (104 mg, 0.233 mmol) in methanol (8 mL) at 0° C. The solution was stirred at 0° C. for 1 h, poured into brine, and extracted with ethyl acetate and ether. The extract was washed with brine, dried (MgSO$_4$), and evaporated. An oily residue was dissolved in hexane/CH$_2$Cl$_2$ and applied on a Sep-Pak cartridge. Hydroxy ketones 10a and 10b (85 mg, 88%) were eluted with hexanelethyl acetate (8:2) as an oil slowly crystallizing in the refrigerator.

10a (major): [α]$^{24}_D$+55° (c 1.17 CHCl$_3$); $^1$H NMR (400 MHz, CDCl$_3$) δ 0.042, 0.065 and 0.074 (3H, 6H and 3H, each s, 4×SiCH$_3$), 0.849 and 0.880 (9H and 9H, each s, 2×Si-t-Bu), 2.28 (1H, m, one of =C—CH$_2$), 2.50 (1H, dd, J=16.2, 5.4 Hz, 2α-H), 2.55-2.70 (3H, m, 2β-H overlapped with one of 6-H and =C—CH$_2$), 2.77 (1H, dd, J=16.2, 2.5 Hz, one of 6-H), 3.62 (1H, dt, J=2.6, 10.2 Hz, one of $CH_2$—$CH_2$—O), 3.85 (1H, m, one of $CH_2$—$CH_2$—O), 4.60 (1H, m, 3β-H), 4.90 (1H, narr m, 5α-H), 5.66 (1H, dd, J=10.5, 6.0 Hz, =CH); $^{13}C$ NMR (125 MHz) δ −5.6 (Si—$CH_3$), −5.4 (Si—$CH_3$), −4.9 (Si—$CH_3$), −4.6 (Si—$CH_3$), 18.0 [$C(CH_3)_3$], 18.5 [$C(CH_3)_3$], 25.7 [C($CH_3)_3$], 26.0 [C($CH_3)_3$], 30.7 ($CH_2$—$CH_2$—C=), 45.1 ($C_2$), 47.9($C_6$), 63.0 ($C_5$), 61.8 (O—$CH_2$—$CH_2$), 70.8 ($C_3$), 127.5 (=$C$—$CH_2$), 142.9 ($C_4$), 208.9 ($C_1$); MS m/z (relative intensity) no M+, 399 ($M^{30}$ −Me, 2), 357 (69), 339 (12), 327 (41), 299 (9), 265 (10), 225 (81), 73 (100); HRMS (ESI) exact mass calcd for $C_{21}H_{42}O_4Si_2Na$ ($M^++Na$) 437.2519, measured 437.2537.

(e) Protection of 5-Hydroxy Group in the Hydroxy Ketone 10a and 10b.

[(3R,5R)-3,5-Bis[(tert-Butyldimethylsilyl)oxy]-4-[3'-[((tert-butyldimethylsilyl)oxy)propylidene]cyclohexanone (12). To a solution of hydroxy ketones 10a and 10b (22 mg, 53 μmol) in anhydrous $CH_2Cl_2$ (0.2 mL) at −50° C. was added 2,6-lutidine (14.5 μL, 124 μmol) and t-butyldimethylsilyl triflate (25 μL, 106 μmol). The mixture was stirred at −50° C., for 50 min. Cold and wet $CH_2CH_2$ was added and the mixture was poured into water and extracted with $CH_2CH_2$. The extract was washed with saturated $CuSO_4$ and water, dried ($MgSO_4$), and evaporated. The oily residue was redissolved in hexane, and purified by flash chromatography on silica. Elution with hexane/ethyl acetate (95:5) gave pure protected ketone 12 as a colorless oil (18 mg, 64%; 74% based on recovered substrates) and a mixture of unreacted 10a and 10b (3 mg).

12: $[α]^{24}_D$ −17° (c 1.35 $CHCl_3$); $^1H$ NMR (500 MHz, CDCl3) δ 0.008 (3H, s, $SiCH_3$), 0.061 (15H, s, 5×$SiCH_3$), 0.833, 0.900 and 0.910 (3×9H, each s, 3×Si-t-Bu), 2.32 (1H, dd, J=14.2, 10.4 Hz, 2α-H), 2.32-2.43 (2H, br m, =C—$CH_2$), 2.43 (1H, dd, J=14.4, 2.8 Hz, 6α-H), 2.52 (1H, ddd, J=14.4, 3.4, 2.2 Hz, 6β-H), 2.75 (1H, ddd, J=14.2, 5.6, 2.2 Hz, 2β-H), 3.65 and 3.71 (each 1H, each m, $CH_2$—$CH_2$—O), 4.76 (1H, ddd, J=10.4, 5.6, 1.7 Hz, 3β-H), 5.01 (1H, ~t, J=3.2 H, 5α-H), 5.70 (1H, dt, J=1.7, 7.6 Hz, =CH); $^{13}C$ NMR (125 MHz) δ −5.27 (Si—$CH_3$), −5.25 (Si—$CH_3$), −5.01 (Si—$CH_3$), −5.00 (Si—$CH_3$), −4.95 (Si—$CH_3$), −4.89 (Si—$CH_3$), 17.9 [$C(CH_3)_3$], 18.3 [$C(CH_3)_3$], 18.4 [$C(CH_3)_3$], 25.6 [C($CH_3)_3$], 25.8 [C($CH_3)_3$], 26.0 [C($CH_3)_3$], 29.7 ($CH_2$—$CH_2$—C=), 50.4 ($C_6$), 52.5 ($C_2$), 62.8 (O—$CH_2$—$CH_2$), 65.9 ($C_3$), 67.9 ($C_5$), 119.1 (=$C$—$CH_2$), 141.1 ($C_4$), 207.5 ($C_1$); MS (EI) m/z (relative intensity) no M+, 513 ($M^+$−Me, 2), 471 (74), 381 (5), 339 (63), 73 (100); exact mass calcd for $C_{27}H_{56}O_4Si_3$ ($M^+$−$C_4H_9$) 471.2782, measured 471.2796.

(f) Preparation of the Allylic Esters 14a and 14b.

[(E)- and (Z)-(3'R,5'R)-3',5'-Bis[(tert-butyldimethylsilyl)oxy]-4'-[3''-[((tert-butyldimethylsilyl)oxy)propylidene]cyclohexylidene]acetic Acid Methyl Esters (14a and 14b). To a solution of diisopropylamine (49 μL, 0.363 mmol) in anhydrous THF (0.37 mL) was added n-BuLi (2.5 M in hexanes, 146 μL, 0.365 mmol) under argon at −78° C. with stirring, and methyl(trimethylsilyl)acetate (60.5 μL, 0.366 mmol) was then added. After 15 min, the ketone 12 (76.5 mg, 0.145 μmol) in anhydrous THF (0.45 mL) was added. The solution was stirred at −78° C. for additional 70 min and the reaction mixture was quenched with wet ether, poured into brine and extracted with ether and benzene. The combined extracts were washed with brine, dried ($MgSO_4$), and evaporated. An oily residue was redissolved in hexane and applied on a Sep-Pak cartridge. Pure allylic esters 14a and 14b (60 mg, 68%; isomer ratio of 14a:14b=ca. 6:1) were eluted with hexane/ethyl acetate (98.5:1.5).

14a (major): $[α]^{24}_D$: −33 (c 0.48 $CHCl_3$); $^1H$ NMR (500 MHz, $CDCl_3$) δ −0.014, 0.054, 0.059, 0.070, 0.080 and 0.109 (each 3H, each s, 6×$SiCH_3$), 0.830, 0.845 and 0.926 (each 9H, each s, 3×Si-t-Bu), 1.87 (1H, ~t, J=12 Hz, 2'α-H), 2.26 (1H, br d, J=13.2 Hz, 6'α-H), 2.33 (1H, br d, J=13.2 Hz, 6'β-H), 2.3-2.4 (2H, m, =C—$CH_2$), 3.6-3.7 (2H, m, $CH_2$—$CH_2$—O), 3.71 (3H, s, $COOCH_3$), 4.15 (1H, ddd, J=12.7, 4.9, 1.5 Hz, 2'β-H), 4.46 (1H, dd, J=10.7, 4.9 Hz, 3'β-H), 4.88 (1H, ~t, J=5'α-H), 5.54 (1H, dt, J=1.5, 7.3 Hz, =CH), 5.65 (1H, br s, 2-H); $^{13}C$ NMR (125 MHz) δ −5.26 (Si—$CH_3$), −5.22 (Si—$CH_3$), −5.14 (Si—$CH_3$), −4.92 (Si—$CH_3$), −4.87 (Si—$CH_3$), −4.77 (Si—$CH_3$), 17.95[$C(CH_3)_3$], 18.38 [$C(CH_3)_3$], 18.41 [$C(CH_3)_3$], 25.6 [C($CH_3)_3$], 25.9 [C($CH_3)_3$], 26.0 [C($CH_3)_3$], 30.8 ($CH_2$—$CH_2$—C=), 40.7 ($C_{6'}$), 46.5 ($C_{2'}$), 50.9 ($CH_3CO$), 63.1 (O—$CH_2$—$CH_2$), 66.5 ($C_{5'}$), 69.6 ($C_{3'}$), 117.0 (=$C$—$CH_2$), 116.9 ($C_2$), 142.7 ($C_4$), 156.0 ($C_{1'}$), 166.6 ($C_1$); minor isomer (Z) selected: 5.50 (1H, dt, J=1.5, 7.3 Hz, =CH), 5.80 (1H, br s, 2-H).

(g) Reduction of the Allylic Esters 14a and 14b.

2-[(E)- and (Z)-(3'R,5'R)-3',5'-Bis[(tert-butyldimethylsilyl)oxy]-4'-[3''-[((tert-butyldimethylsilyl)oxy)propylidene]cyclohexylidene]ethanol (16a and 16b). Diisobutylaluminum hydride (1.0 M in hexane, 616 μL, 616 μmol) was slowly added to a stirred solution of the allylic esters 14a and 14b (6:1, 60 mg, 103 μmol) in toluene/methylene chloride (2:1, 2.25 mL) at −78° C. under argon. Stirring was continued at −78° C. for 1 h, the mixture was quenched by addition of potassium sodium tartrate (2 N, 2 mL), aq. HCl (2 N, 2 mL) and $H_2O$ (24 mL), and then diluted with ether and benzene. The organic layer was washed with diluted $NaHCO_3$ and brine, dried ($MgSO_4$), and evaporated. The residue was purified by flash chromatography. Elution with hexane/ethyl acetate (95:5) resulted in 49 mg of mixture of products 16a and 16b, yield 86%). Analytical samples of both isomers were obtained after HPLC (10 mm×25 cm Zorbax-Sil column, 4 mL/min) using hexane/ethyl acetate (9:1) solvent system. Pure oily compounds 16a and 16b were eluted at $R_V$ 28 mL and 29 mL, respectively.

16a (major): $^1H$ NMR (500 MHz, $CDCl_3$) δ −0.016, 0.055, 0.059, and 0.068 (3H, 6H, 6H and 3H, each s, 6×$SiCH_3$), 0.831, 0.888 and 0.911 (each 9H, each s, 3×Si-t-Bu), 1.80 (1H, t, J=11.8 Hz, 2'α-H), 2.16 (1H, br d, J=13.2 Hz, 6'α-H), 2.26 (1H, br d, J=13.2 Hz, 6'β-H), 2.34 (2H, m, =C—$CH_2$), 2.86 (1H, ddd, J=12.4, 4.4, 1.5 Hz, 2'β-H), 3.62 (2H, m, $CH_2$—$CH_2$—O), 4.19 (2H, t, J~6 Hz; after $D_2O$: d, J=7.0 Hz, 1-H), 4.37 (1H, after $D_2O$: dm, J=10.4 Hz, 3'β-H), 4.80 (1H, ~t, J=3 Hz, 5'α-H), 5.47 (2H, m, 2×=CH); $^{13}C$ NMR (125 MHz) δ −5.28 (2×Si—$CH_3$), −5.06 (Si—$CH_3$), −5.00 (Si—$CH_3$), −4.85 (Si—$CH_3$), −4.79 (Si—$CH_3$), 18.0 [$C(CH_3)_3$], 18.4 [2×$C(CH_3)_3$], 25.6 [C($CH_3)_3$], 25.9 [C($CH_3)_3$], 26.0 [C($CH_3)_3$], 30.8 ($CH_2$—$CH_2$—C=), 40.0 ($C_{2'}$), 45.5 ($C_{6'}$), 58.7 ($C_1$), 63.2 (O—$CH_2$—$CH_2$), 66.5 ($C_{5'}$), 70.0 ($C_{3'}$), 116.6 (=$C$—$CH_2$), 125.4 ($C_2$), 137.2 ($C_{1'}$), 143.4 ($C_{4'}$); MS (EI) m/z (relative intensity) no M+, 538 ($M^+$−$H_2O$, 9), 499 (12), 471 (7), 424 (39), 407 (11), 349 (23), 73 (100), HRMS (ESI) exact mass calcd for $C_{29}H_{60}O_4Si_3Na$ ($M^++Na$) 579.3697, measured 579.3704.

16b (minor): $^1H$ NMR (500 MHz, $CDCl_3$) δ 0.029, 0.055, 0.060, 0.064 and 0.069 (3H, 6H, 3H, 3H and 3H, each s, 6×$SiCH_3$), 0.849, 0.898 and 0.918 (each 9H, each s, 3×Si-t-Bu), 1.87 (1H, br d, J=13.8 Hz, 2'β-H), 2.03 (1H, br t, J=11.5 Hz, 6'β-H), 2.34 (2H, m, =C—$CH_2$), 2.51 (1H, ddd, J=12.0, 5.0, 1.6 Hz, 6'α-H), 2.76 (1H, br d, J=13.8 Hz, 2'α-H), 3.64 (2H, m, $CH_2$—$CH_2$—O), 4.02 and 4.13 (1H and 1H, each m; after $D_2O$: each dd, J=11.8, 7.2 Hz, $CH_2$—OH), 4.39 (1H, dm, J=10.6 Hz, 5'α-H), 4.89 (1H, br s, 3β-H), 5.52 (1H, dt, J=1.3, 7.5 Hz, =$CH$—$CH_2$), 5.71 (1H, t, J=7.2 Hz, =C H—CH₂—OH); MS (EI) m/z (relative intensity) no M⁺, 538 (M⁺–H₂O, 4), 499 (6), 471 (4), 424 (12), 407 (6), 349 (11), 73 (100); HRMS (ESI) exact mass calcd for $C_{29}H_{60}O_4Si_3$ (M⁺–H₂O) 538.3694, measured 538.3689.

(h) Conversion of the Allylic Alcohols 16a and 16b into Phosphine Oxides 18a and 18b.

2-[(E)- and (Z)-(3'R,5'R)-3',5'-Bis[[(tert-butyldimethylsilyl)oxy]-4'-[3"-[((tert-butyldimethylsilyl)oxy)propylidene]cyclohexylidene]ethyl]-diphenylphosphine Oxides (18a and 18b). To the allylic alcohols 16a and 16b (5.5:1, 40.5 mg, 70.2 μmol) in anhydrous THF (0.8 mL) was added n-BuLi (2.5 M in hexanes, 35 μL, 87.5 μmol) under argon at 0° C. with stirring. Freshly recrystallized tosyl chloride (14.0 mg, 73 μmol) was dissolved in anhydrous THF (190 μL) and added to the allylic alcohol-BuLi solution. The mixture was stirred at 0° C. for 5 min and set aside at 0 (C. In another dry flask with air replaced by argon, n-BuLi (2.5 M in hexanes, 140 μL, 0.35 mmol) was added to $Ph_2PH$ (62 μL, 0.34 mmol) in anhydrous THF (420 μL) at 0° C. with stirring. The red solution was siphoned under argon pressure to the solution of tosylate until the orange color persisted (ca. ¼ of the solution was added). The resulting mixture was stirred an additional 40 min at 0° C., and quenched by addition of H₂O (40 μl). Solvents were evaporated under reduced pressure and the residue was dissolved in methylene chloride (1.0 mL) and stirred with 10% H₂O₂ (0.5 mL) at 0° C. for 1 h. The organic layer was separated, washed with cold aq. sodium sulfite and H₂O, dried (MgSO₄), and evaporated. The residue was subjected to flash chromatography. Elution with hexane/ethyl acetate (95:5) gave unchanged allylic alcohols (16.3 mg). Subsequent elution with hexane/ethyl acetate (7:3) resulted in mixture of products: 18a and 18b (25 mg, 49%; 81% based on recovered substrates 16a,b).

18a (major isomer): ¹H NMR (500 MHz, CDCl₃) δ –0.044, –0.022, 0.011, 0.020, 0.030, and 0.035 (each 3H, each s, 6×SiCH₃), 0.787, 0.878 and 0.894 (each 9H, each s, 3×Si-t-Bu), 1.47 (1H, br t, J~11 Hz, 2'α-H), 2.04 (1H, m, 6'α-H), 2.22 (1H, d, J=13.7 Hz, 6'β-H), 2.28 (2H, m, =C—C$\underline{H}_2$—CH₂), 2.62 (1H, dd, J=12.8, 4.2 Hz, 2'β-H), 3.58 (2H, m, CH₂—C$\underline{H}_2$—O), 4.32 (1H, dm, J~10 Hz, 3'β-H), 3.17 (2H, dd, J=15.2, 7.6 Hz, CH₂—PO), 4.73 (1H, br s, 5'α-H), 5.27 (1H, m, =C$\underline{H}$—CH₂—CH₂), 5.43 (1H, br t, J~7 Hz, =C$\underline{H}$—CH₂—PO), 7.46, 7.51 and 7.72 (4H, 2H and 4H, each m, Ar—H); HRMS (ESI) exact mass calcd for $C_{41}H_{69}O_4Si_3PNa$ (M⁺+Na) 763.4139, measured 763.4157.

Wittig-Horner Coupling of Protected 25-Hydroxy Grundmann's Ketone 19a with the Phosphine Oxides 18a and 18b (SCHEME III).

1α-[(tert-Butyldimethylsilyl)oxy]-2-[3'-[((tert-butyldimethylsilyl)oxy)propylidene]-25-[(triethylsilyl)oxy]-19-norvitamin $D_3$ tert-Butyldimethylsilyl Ethers (22a and 22b). To a solution of phosphine oxides 18a and 18b (6:1, 20.3 mg, 27.6 μmol) in anhydrous THF (0.3 mL) at –78° C. was slowly added phenyllithium (1.56 M in cyclohexane, 19 μL, 30 μmol) under argon with stirring. The solution turned deep orange. The mixture was stirred at –78° C. for 20 min and a precooled (–78° C.) solution of protected hydroxy ketone 19a (15.4 mg, 39 μmol), prepared according to published procedure [Sicinski et al., J. Med. Chem. 37, 3730 (1994)], in anhydrous THF (80 μL) was slowly added. The mixture was stirred under argon at –78° C. for 3 h and at 6° C. for 19 h. Ethyl acetate, benzene and water were added, and the organic phase was washed with brine, dried (MgSO₄), and evaporated. The residue was redissolved in hexane and applied on a silica column. Elution with hexane/ethyl acetate (99.5:0.5) yielded 19-norvitamin derivatives 22a and 22b (8.6 mg, 47% based on recovered substrates). The column was then washed with hexane/ethyl acetate (96:4) to recover some unchanged C,D-ring ketone 19a (7 mg), and with ethyl acetate to recover unreacted diphenylphosphine oxide (5.5 mg). Analytical sample of the main product 22a was obtained by HPLC (10 mm×25 cm Zorbax-Sil column, 4 mL/min) purification using hexane/ethyl acetate (99.8:0.2) solvent system. Pure compound 22a was eluted at $R_V$ 28 mL as a colorless oil. 22a: UV (in EtOH) $\lambda_{max}$ 244.0, 252.5, 262.5 nm; ¹H NMR (500 MHz, CDCl₃) δ –0.023, 0.052, 0.056, 0.061, 0.063, and 0.070 (each 3H, each s, 6×SiCH₃), 0.555 (3H, s, 18-H₃), 0.565 (6H, q, J=7.9 Hz, 3×SiCH₂), 0.819, 0.897, and 0.923 (9H and 9H, each s, 3×Si-t-Bu), 0.878 (3H, d, J=7.1 Hz, 21-H₃), 0.947 (9H, t, J=7.9 Hz, 3×SiCH₂C$\underline{H}_3$), 1.190 and 1.191 (3H and 3H, each s, 26- and 27-H₃), 1.79 (1H, t, J=11.6 Hz, 10α-H), 1.90 (1H, m), 2.00 (2H, m), 2.19 (1H, br d, J~14 Hz, 4β-H), 2.27 (1H, br d, J~14 Hz, 4α-H), 2.33 (2H, m, =CH—C$\underline{H}_2$), 2.79 (1H, br d, J~13 Hz, 9β-H), 3.05 (1H, dd, J=12.0, 4.0 Hz, 10β-H), 3.62 (2H, m, CH₂—C$\underline{H}_2$—O), 4.34 (1H, m, w/2=20 Hz, 1β-H), 4.81 (1H, t, J~2.8 Hz, 3α-H), 5.47 (1H, dt, J~1.5, ~7.5 Hz, $\underline{H}$C=C—CH₂), 5.88 and 6.12 (1H and 1H, each d, J=11.0 Hz, 7- and 6-H); HRMS (ESI) exact mass calcd for $C_{53}H_{104}O_4Si_4Na$ (M⁺+Na) 939.6909, measured 939.6900.

(j) (20S)-1α-[(tert-Butyldimethylsilyl)oxy]-2-[3'-[((tert-butyldimethylsilyl)oxy)propylidene]-25-[(triethylsilyl)oxy]-19-norvitamin $D_3$ tert-Butyldimethylsilyl Ethers (23a and 23b).

Protected 19-norvitamin $D_3$ compounds 23a and 23b were obtained by Wittig-Horner coupling of protected 25-hydroxy Grundmann's ketone 19b with the phosphine oxides 18a and 18b performed analogously to the process described above for the preparation of (20R)-isomers 22a and 22b. The protected vitamins were purified on a silica column, using hexane/ethyl acetate (99.5:0.5) solvent system, and they were obtained in ca. 47% yield. Analytical sample of the protected vitamin 23a was obtained by HPLC (10 mm×25 cm Zorbax-Sil column, 4 mL/min) purification using hexane/ethyl acetate (99.7:0.3) solvent system. Pure compound 23a was eluted at $R_V$ 25 mL as a colorless oil. 23a: UV (in EtOH) $\lambda_{max}$ 243.5, 252.5, 262.5 nm; ¹H NMR (500 MHz, CDCl₃) δ –0.024, 0.057, 0.059, and 0.069 (3H, 3H, 6H, and 6H, each s, 6×SiCH₃), 0.550 (3H, s, 18-H₃), 0.560 (6H, q, J=7.5 Hz, 3×SiCH₂), 0.818, 0.895, and 0.923 (each 9H, each s, 3×Si-t-Bu), 0.867 (3H, d, J=7.0 Hz, 21-H₃), 0.943 (9H, t, J=7.5 Hz, 3×SiCH₂C$\underline{H}_3$), 1.191 (6H, s, 26- and 27-H₃), 1.79 (1H, t, J~12 Hz, 10α-H), 1.90 (1H, m), 2.00 (2H, m), 2.19 (1H, br d, J~13 Hz, 4β-H), 2.27 (1H, br d, J~13 Hz, 4α-H), 2.33 (2H, m, =CH—C$\underline{H}_2$), 2.79 (1H, br d, J~11.5 Hz, 9β-H), 3.05 (1H, dm, J~12 Hz, 10β-H), 3.62 (2H, m, CH₂—C$\underline{H}_2$—O), 4.34 (1H, m, w/2=20 Hz, 1β-H), 4.80 (1H, br s, 3α-H), 5.47 (1H, t, J=7.0 Hz, $\underline{H}$C=C—CH₂), 5.88 and 6.11 (1H and 1H, each d, J=11.2 Hz, 7- and 6-H); HRMS (ESI) exact mass calcd for $C_{53}H_{104}O_4Si_4Na$ (M⁺+Na) 939.6909, measured 939.6907.

(k) Hydrolysis of the Silyl Protecting Groups in the 19-Norvitamin $D_3$ Derivatives 22a and 22b.

1α,25-Dihydroxy-2-[3'-hydroxypropylidene]-19-norvitamin $D_3$ (24a and 24b). To a solution of the protected vitamins 22a and 22b (5.7 mg, 6.2 μmol) in anhydrous THF (4.3 mL) was added tetrabutylammonium fluoride (1.0 M in THF, 372 μL, 372 μmol). The mixture was stirred under argon at room temperature for 18 h, poured into brine and extracted with ethyl acetate and diethyl ether. Organic extracts were washed with brine, dried (MgSO₄), and evaporated. The residue was purified by HPLC (10 mm×25 cm Zorbax-Sil column, 4 mL/min) using hexane/2-propanol (8:2) solvent system. Pure mixture of 19-norvitamin 24a and 24b was collected at $R_V$ 37.5 mL. Separation of both isomers was easily achieved by reversed-phase HPLC (6.2 mm×25 cm Zorbax-ODS column, 2 mL/min) using methanol/water (8:2) solvent system. Analytically pure E-isomer 24a (2.8 mg, 97%) was collected at $R_V$ 23 mL and Z-isomer 24b (11 μg) at $R_V$ 29 mL.

24a: UV (in EtOH) $\lambda_{max}$ 243.0, 251.0, 261.5 nm; $^1$H NMR (500 MHz, CDCl$_3$) δ 0.549 (3H, s, 18-H$_3$), 0.940 (3H, d, J=6.3 Hz, 21-H$_3$), 1.22 (6H, s, 26- and 27-H$_3$), 2.33 and 2.55 (1H and 1H, each m, =CH—C$\underline{H}_2$), 2.47 (2H, narr mn, 4α- and 4β-H), 2.82 (1H, br d, J~13 Hz, 9β-H), 3.16 (1H, dd, J=13.0, 4.8 Hz, 10β-H), 3.66 and 3.76 (1H and 1H, each m, CH$_2$—C$\underline{H}_2$—O), 4.45 (1H, m, w/2=20 Hz, 1β-H), 4.85 (1H, narr m, 3α-H), 5.66 (1H, t, J=7.3 Hz, $\underline{H}$C=C—CH$_2$), 5.88 and 6.31 (1H and 1H, each d, J=11.2 Hz, 7- and 6-H); HRMS (ESI) exact mass calcd for C$_{29}$H$_{48}$O$_4$Na (M$^+$+Na) 483.3450, measured 483.3461.

24b: UV (in EtOH) $\lambda_{max}$ 243.0, 251.5, 262.0 nm; $^1$H NMR (800 MHz, CDCl$_3$) δ 0.553 (3H, s, 18-H$_3$), 0.939 (3H, d, J=6.6 Hz, 21-H$_3$), 1.22 (6H, s, 26- and 27-H$_3$), 2.19 (1H, t, J=11.0 Hz, 4β-H), 2.25 (1H, br d, J=14.6 Hz, 10β-H), 2.40 and 2.56 (1H and 1H, each m, =CH—C$\underline{H}_2$), 2.74 (1H, dd, J=13.0, 4.8 Hz, 4α-H), 2.81 (1H, br d, J=12.5 Hz, 9β-H), 2.93 (1H, dd, J=14.6, 3.8 Hz, 10α-H), 3.67 and 3.76 (1H and 1H, each m, CH$_2$—C$\underline{H}_2$—O), 4.48 (1H, m, w/2=19 Hz, 3α-H), 4.89 (1H, narr m, 1β-H), 5.65 (1H, t, J=8.1 Hz, $\underline{H}$C=C—CH$_2$), 5.85 and 6.40 (1H and 1H, each d, J=11.0 Hz, 7- and 6-H).

(l) Hydrolysis of the Silyl Protecting Groups in the 19-Norvitamin D$_3$ Derivatives 22a and 22b.

(20S)-1α,25-Dihydroxy-2-[3'-hydroxypropylidene]-19-norvitamin D$_3$ (24a and 24b). Vitamins 25a and 25b were obtained by hydrolysis of the silyl protecting groups in the 19-norvitamin derivatives 23a and 23b performed analogously to the process described above for the preparation of (20R)-isomers 24a and 24b. The residue was purified by HPLC (10 mm×25 cm Zorbax-Sil column, 4 mL/min) using hexane/2-propanol (8:2) solvent system. Pure mixture of 19-norvitamin 25a and 25b (95% yield) was collected at $R_V$ 36.5 mL. Separation of both isomers was easily achieved by reversed-phase HPLC (6.2 mm×25 cm Zorbax-ODS column, 2 mL/min) using methanol/water (8:2) solvent system. Analytically pure E-isomer 25a was collected at $R_V$ 18 mL and Z-isomer 25b at $R_V$ 28 mL (ratio of 25a:25b=160:1).

25a: UV (in EtOH) $\lambda_{max}$ 243.0, 251.5, 261.0 nm; $^1$H NMR (500 MHz, CDCl$_3$) δ 0.548 (3H, s, 18-H$_3$), 0.858 (3H, d, J=6.4 Hz, 21-H$_3$), 1.21 (6H, s, 26- and 27-H$_3$), 2.35 and 2.54 (1H and 1H, each m, =CH—C$\underline{H}_2$), 2.47 (2H, narr m, 4α- and 4β-H), 2.82 (1H, br d, J=12.7 Hz, 9β-H), 3.16 (1H, dd, J=13.1, 4.9 Hz, 10β-H), 3.65 and 3.76 (1H and 1H, each m, CH$_2$—C$\underline{H}_2$—O), 4.45 (1H, m, w/2=25 Hz, 1β-H), 4.85 (1H, narr m, 3α-H), 5.66 (1H, t, J=7.4 Hz, $\underline{H}$C=C—CH$_2$), 5.88 and 6.31 (1H and 1H, each d, J=11.4 Hz, 7- and 6-H); HRMS (ESI) exact mass calcd for C$_{29}$H$_{48}$O$_4$Na (M$^+$+Na) 483.3450, measured 483.3427.

25b: UV (in EtOH) $\lambda_{max}$ 243.0, 251.5, 262.0 nm; $^1$H NMR (800 MHz, CDCl$_3$) δ 0.550 (3H, s, 18-H$_3$), 0.854 (3H, d, J=6.6 Hz, 21-H$_3$), 1.21 (6H, s, 26- and 27-H$_3$), 2.19 (1H, t, J~12 Hz, 4β-H), 2.24 (1H, br d, J=14.6 Hz, 10β-H), 2.40 and 2.56 (1H and 1H, each m, =CH—C$\underline{H}_2$), 2.74 (1H, dd, J=13.2, 4.4 Hz, 4α-H), 2.82 (1H, br d, J=12.4 Hz, 9β-H), 2.92 (1H, dd, J=14.6, 3.7 Hz, 10α-H), 3.61 and 3.72 (1H and 1H, each m, CH$_2$—C$\underline{H}_2$—O), 4.47 (1H, m, w/2=18 Hz, 3α-H), 4.88 (1H, narr m, 1β-H), 5.65 (1H, t, J~7.5 Hz, $\underline{H}$C=C—CH$_2$), 5.85 and 6.40 (1H and 1H, each d, J=11.0 Hz, 7- and 6-H).

SCHEME I

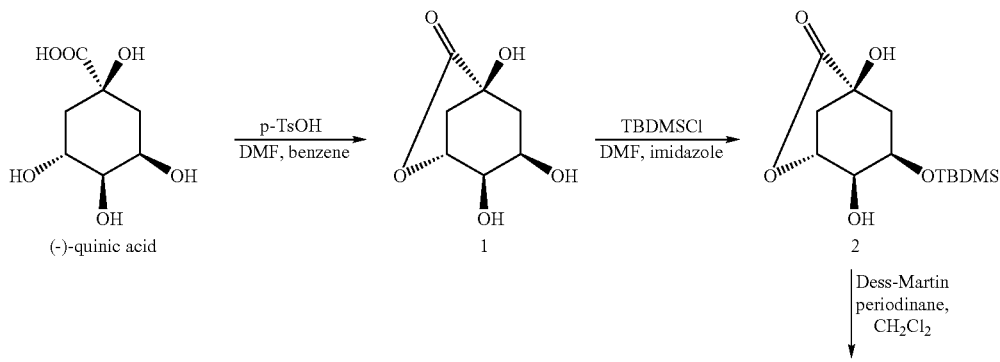

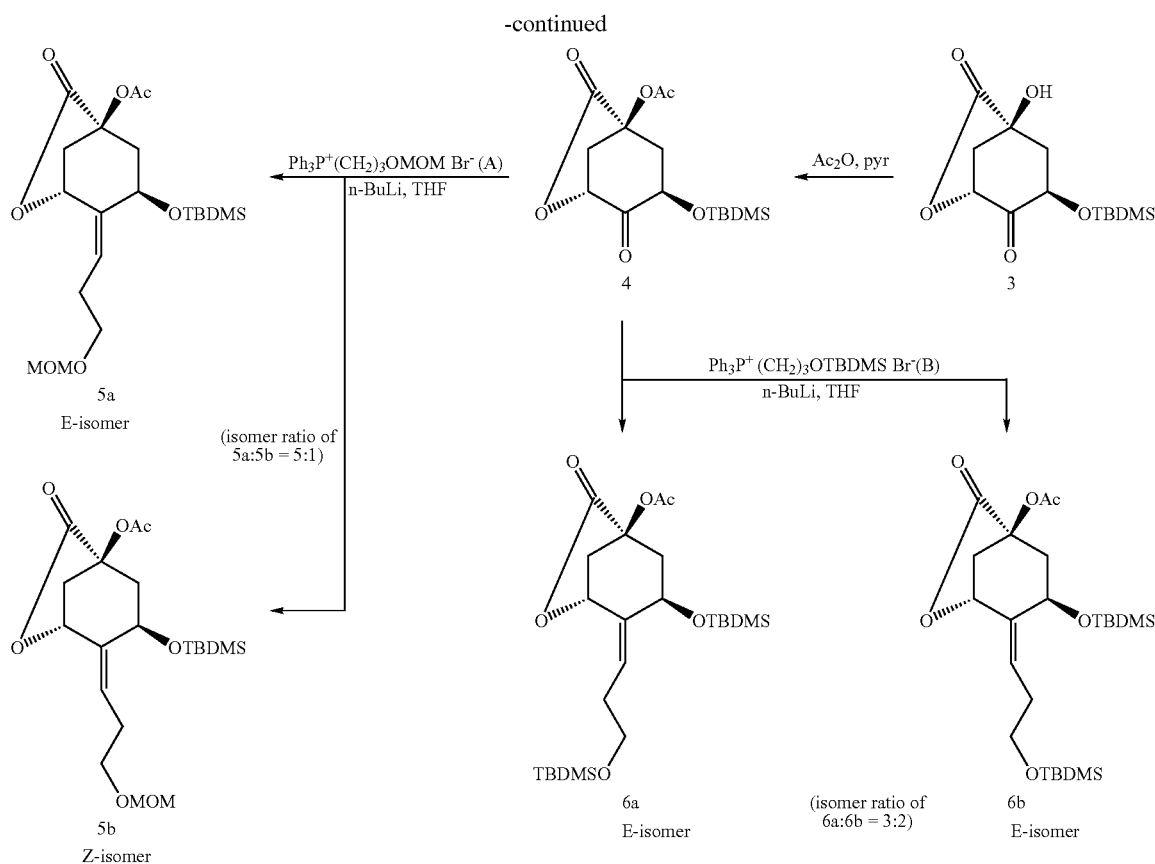
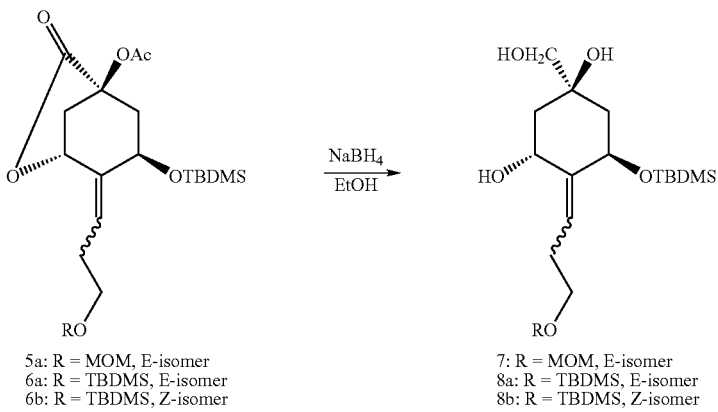
SCHEME II
5a: R = MOM, E-isomer
6a: R = TBDMS, E-isomer
6b: R = TBDMS, Z-isomer
7: R = MOM, E-isomer
8a: R = TBDMS, E-isomer
8b: R = TBDMS, Z-isomer
$NaIO_4$
$CH_3OH$ -continued
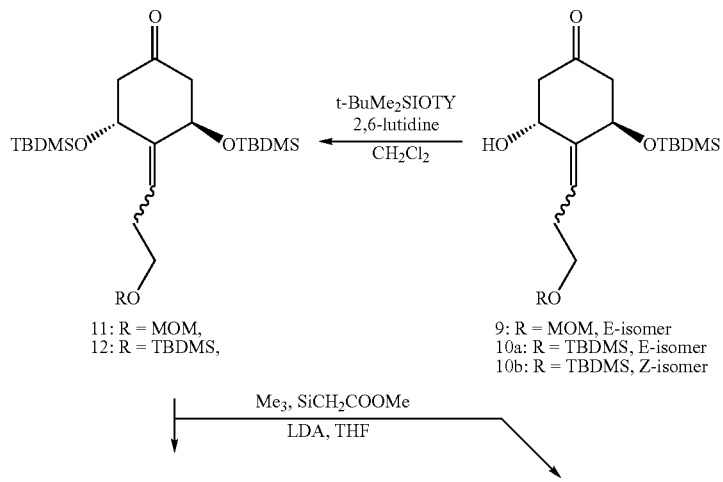
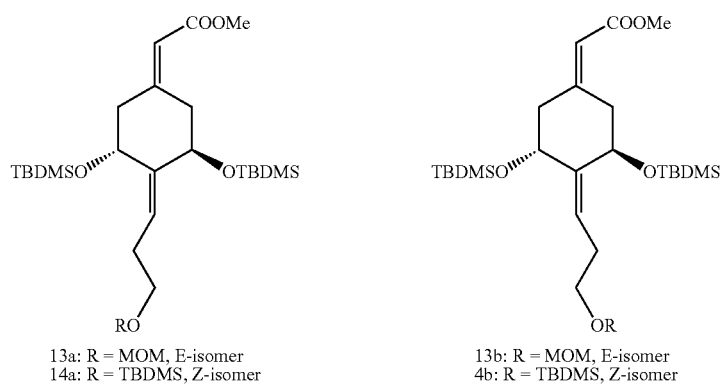
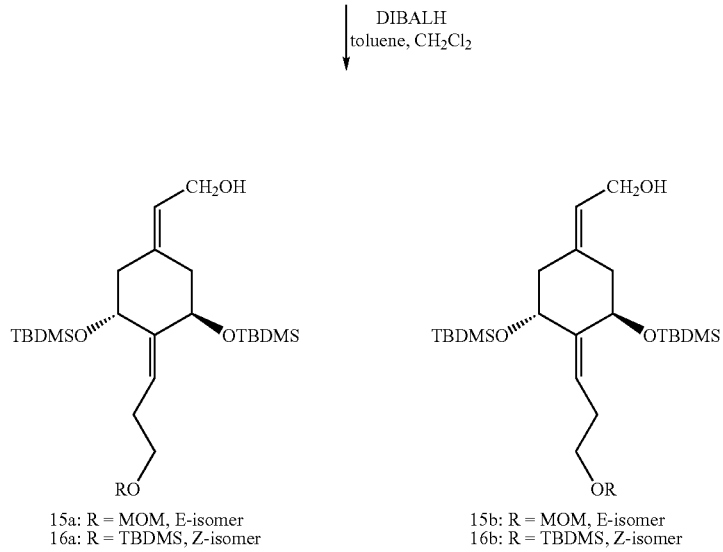

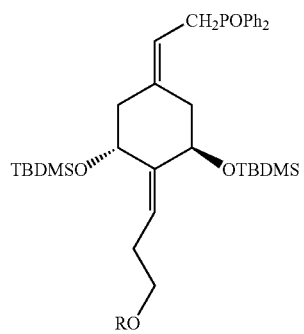
17a: R = MOM, E-isomer
18a: R = TBDMS, Z-isomer
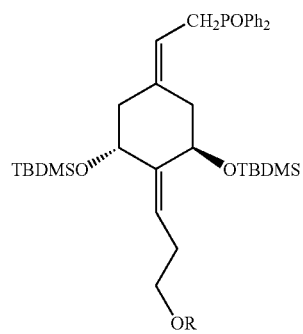
17b: R = MOM, E-isomer
18b: R = TBDMS, Z-isomer
SCHEME III
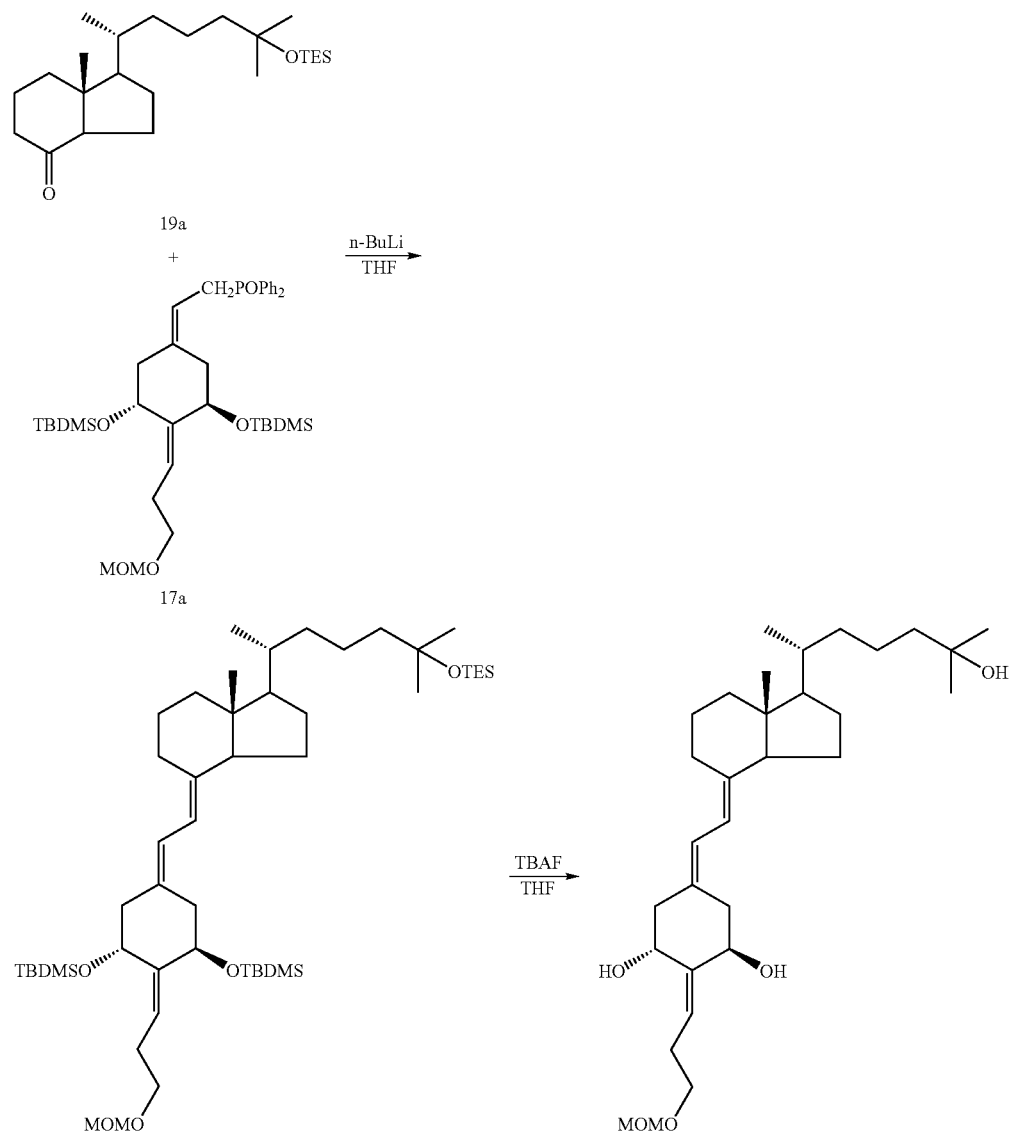

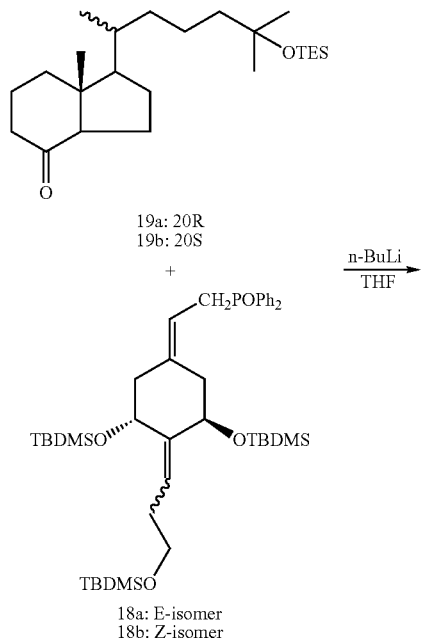
19a: 20R
19b: 20S
18a: E-isomer
18b: Z-isomer
n-BuLi / THF
-continued
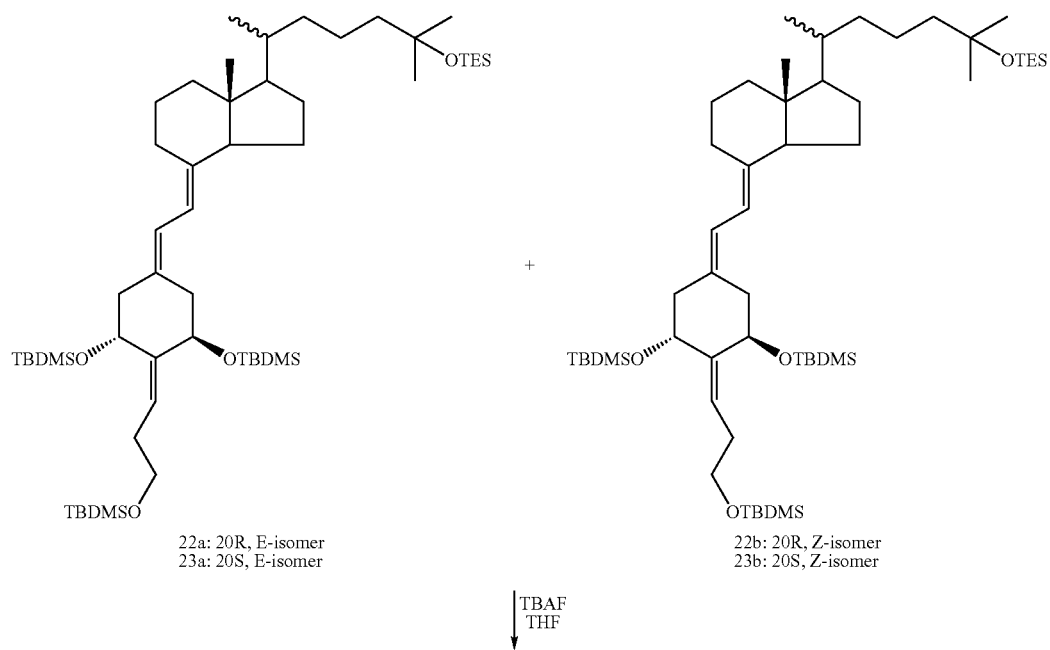
22a: 20R, E-isomer
23a: 20S, E-isomer
22b: 20R, Z-isomer
23b: 20S, Z-isomer
TBAF / THF -continued

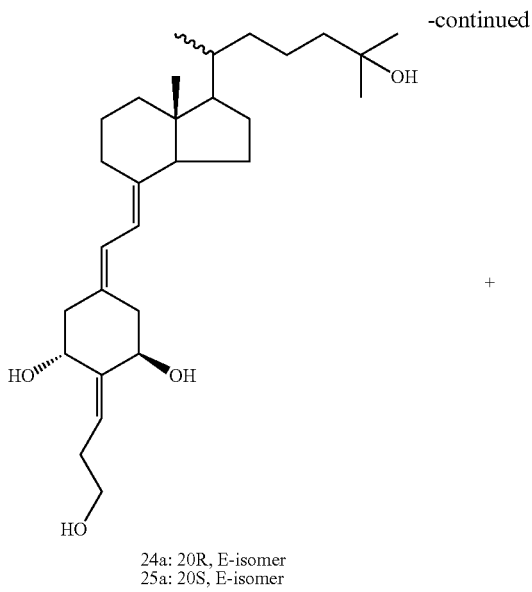

24a: 20R, E-isomer
25a: 20S, E-isomer

+

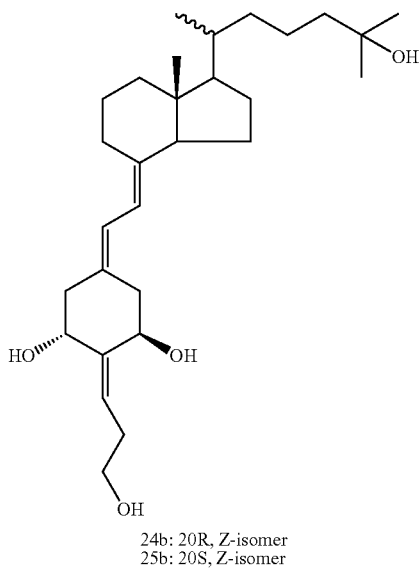

24b: 20R, Z-isomer
25b: 20S, Z-isomer

For treatment purposes, the novel compounds of this invention defined by formula I may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically-acceptable and non-toxic excipients such as stabilizers, anti-oxidants, binders, coloring agents or emulsifying or taste-modifying agents.

The compounds may be administered orally, topically, parenterally or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. Doses of from 0.01 µg to 100 µg per day of the compounds, preferably from about 0.1 µg/day to about 50 µg/day, are appropriate for treatment purposes, such doses being adjusted according to the disease to be treated, its severity and the response of the subject as is well understood in the art. Since the new compounds exhibit specificity of action, each may be suitably administered alone, or together with graded doses of another active vitamin D compound—e.g. 1α-hydroxyvitamin $D_2$ or $D_3$, or 1α,25-dihydroxyvitamin $D_3$—in situations where different degrees of bone mineral mobilization and calcium transport stimulation is found to be advantageous.

Compositions for use in the above-mentioned treatment of psoriasis and other malignancies comprise an effective amount of one or more 2-propylidene-19-nor-vitamin D compound as defined by the above formula I as the active ingredient, and a suitable carrier. An effective amount of such compounds for use in accordance with this invention is from about 0.01 µg to about 100 µg per gm of composition, preferably from about 0.1 µg/gm to about 50 µg/gm of the composition, and may be administered topically, transdermally, orally or parenterally in dosages of from about 0.01 µg/day to about 100 µg/day, preferably from about 0.1 µg/day to about 50 µg/day.

The compounds may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain in addition other pharmaceutically innocuous or beneficial components, such as stabilizers, antioxidants, emulsifiers, coloring agents, binders or taste-modifying agents.

The compounds are advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For asthma treatment, inhalation of powder, self-propelling or spray formulations, dispensed with a spray can, a nebulizer or an atomizer can be used. The formulations, when dispensed, preferably have a particle size in the range of 10 to 100μ.

The formulations may conveniently be presented in dosage unit form and may be prepared by any of the methods well known in the art of pharmacy. By the term "dosage unit" is meant a unitary, i.e. a single dose which is capable of being administered to a patient as a physically and chemically stable unit dose comprising either the active ingredient as such or a mixture of it with solid or liquid pharmaceutical diluents or carriers.

2-propylidene-19-nor Slow Release Compounds

Modified vitamin D compounds that exhibit a desirable and highly advantageous pattern of biological activity in vivo, namely, the more gradual onset and more prolonged duration of activity, may also be used herein.

Structurally, the key feature of the modified vitamin D compounds having these desirable biological attributes is that they are derivatives of 2-propylidene-19-nor-vitamin D analogs, in which a hydrolyzable group is attached to the hydroxy group at carbon 25 and, optionally, to any other of the hydroxy groups present in the molecule. Depending on various structural factors—e.g. the type, size, structural complexity—of the attached group, these derivatives hydrolyze to the active 2-propylidene-19-nor-vitamin D analog, at different rates in vivo, thus providing for the "slow release" of the biologically active vitamin D compound in the body.

The "slow release" in vivo activity profiles of such compounds can, of course, be further modulated by the use of mixtures of derivatives or the use of mixtures consisting of one or more vitamin D derivative together with underivatized vitamin D compounds.

It is important to stress that the critical structural feature of the vitamin derivatives identified above is the presence of a hydrolyzable group attached to the hydroxy group at carbon 25 of the molecule. The presence of a hydrolyzable group at that position imparts on the resulting derivatives the desirable "slow-release" biological activity profile mentioned above. Other hydroxy functions occurring in the molecule (e.g. hydroxy functions at carbons 1 or 3) may be present as free hydroxy groups, or one or more of them may also be derivatised with a hydrolyzable group.

The "hydrolyzable group" present in the above-mentioned derivatives is preferably an acyl group, i.e. a group of the type $Q^1CO$—, where $Q^1$ represents hydrogen or a hydrocarbon radical of from 1 to 18 carbons that may be straight chain, cyclic, branched, saturated or unsaturated. Thus, for example, the hydrocarbon radical may be a straight chain or branched alkyl group, or a straight chain or branched alkenoyl group with one or more double bonds, or it may be an optionally substituted cycloalkyl or cycloalkenyl group, or an aromatic group, such as substituted or unsubstituted phenyl, benzyl or naphthyl. Especially preferred acyl groups are alkanoyl or alkenoyl groups, of which some typical examples are formyl, acetyl, propanoyl, hexanoyl, isobutyryl, 2-butenoyl, palmitoyl or oleoyl. Another suitable type of hydrolyzable group is the hydrocarbyloxycarbonyl group, i.e. a group of the type $Q^2$-O—CO—, where $Q^2$ is a $C_1$ to $C_{18}$ hydrocarbon radical as defined above. Exemplary of such hydrocarbon radicals are methyl, ethyl, propyl, and higher straight chain or branched alkyl and alkenoyl radicals, as well as aromatic hydrocarbon radicals such as phenyl or benzoyl.

These modified vitamin D compounds are hydrolyzable in vivo to the active analog over a period of time following administration, and as a consequence regulate the in vivo availability of the active analog, thereby also modulating their activity profile in vivo. The term "activity profile" refers to the biological response over time of vitamin D compounds. Individual modified compounds, or mixtures of such compounds, can be administered to "fine tune" a desired time course of response.

As used herein the term "modified vitamin D compound" encompasses any vitamin D compound in which one or more of the hydroxy functions present in such a compound are modified by derivatization with a hydrolyzable group. A "hydrolyzable group" is a hydroxy-modifying group that can be hydrolyzed in vivo, so as to regenerate the free hydroxy functions.

In the context of this disclosure, the term hydrolyzable group preferably includes acyl and hydrocarbyloxycarbonyl groups, i.e. groups of the type $Q^1CO$— and $Q^2$-O—CO, respectively, where $Q^1$ and $Q^2$ have the meaning defining earlier.

Structurally, the modified vitamin D compounds encompassed may be represented by the formula XI shown below:

XI 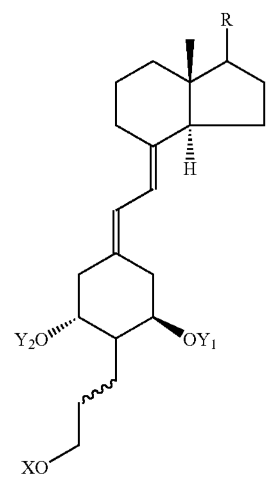 where $Y_1$, $Y_2$, and R are as previously defined herein with respect to formula I with the exception that $R^5$ in the side chain is —$OY_3$ and $Y_3$ is an acyl group or a hydrocarbyloxycarbonyl group, as previously defined herein.

Some specific examples of such modified vitamin D compounds include 2-propylidene-19-nor vitamin D derivatives such as:

2-(3'-hydroxypropylidene)-19-nor-1α,25$(OH)_2$-$D_3$-1,3,25-Triacetate where $Y_1$=$Y_2$=$Y_3$ and is $CH_3CO$;

2-(3'-hydroxypropylidene)-19-nor-1α,25$(OH)_2$-$D_3$-1,3,25-Trihexanoate where $Y_1$=$Y_2$=$Y_3$ and is $CH_3(CH_2)_4CO$;

2-(3'-hydroxypropylidene)-19-nor-1α,25$(OH)_2$-$D_3$-1,3,25-Trinonanoate where $Y_1$=$Y_2$=$Y_3$ and is $CH_3(CH_2)_7CO$;

2-(3'-hydroxypropylidene)-19-nor-1α,25$(OH)_2$-$D_3$-25-Acetate where $Y_1$=and is H and $Y_3$ is $CH_3CO$.

These compounds can be prepared by known methods. See for example U.S. Pat. No. 5,843,927.

Biological Activity of 2-propylidene-19-nor-vitamin D Compounds

Figure 2:
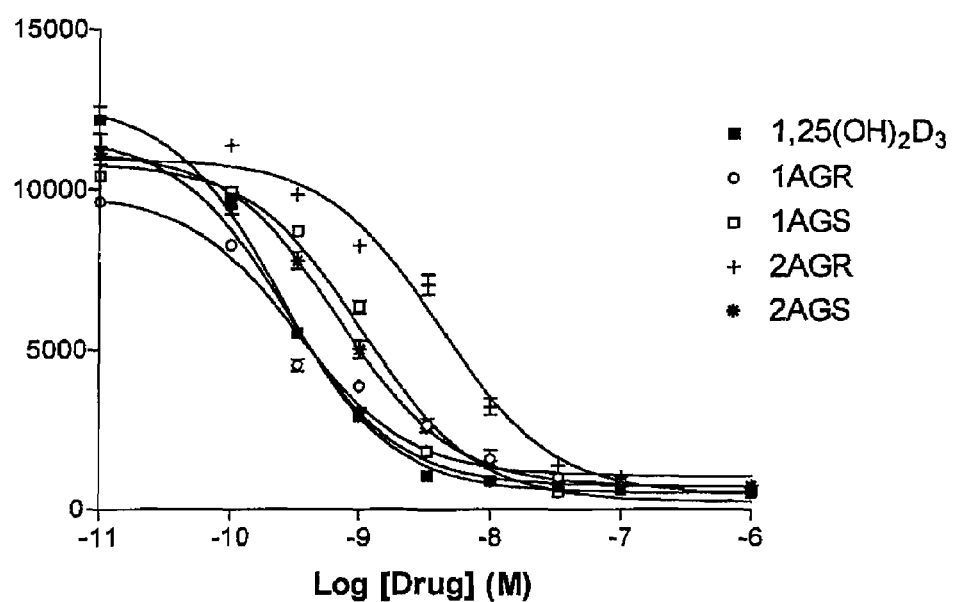
FIG. 2 is a graph illustrating the relative activity of 1α,25-dihydroxyvitamin $D_3$ as well as the herein described and claimed E-isomer of 2-(3'-hydroxypropylidene)-19-nor-1α,25-$(OH)_2D_3$ (1AGR), the E-isomer of 2-(3'-hydroxypropylidene)-19-nor-(20S)-1α,25-$(OH)_2D_3$ (1AGS), the Z-isomer of 2-(3'-hydroxypropylidene)-19-nor-1α,25-$(OH)_2D_3$ (2AGR), and the Z-isomer of 2-(3'-hydroxypropylidene)-19-nor-1α,25-$(OH)_2D_3$ (2AGS)

FIGS. 1 and 2—Competitive VDR Binding

Competitive binding of the analogs to the porcine intestinal receptor was carried out by the method described by Dame et al (Biochemistry 25, 4523-4534, 1986), except the recombinantly produced rat receptor was used as the receptor (see Vanhooke et al., Biochemistry, in press, 2004).

Figure 3:
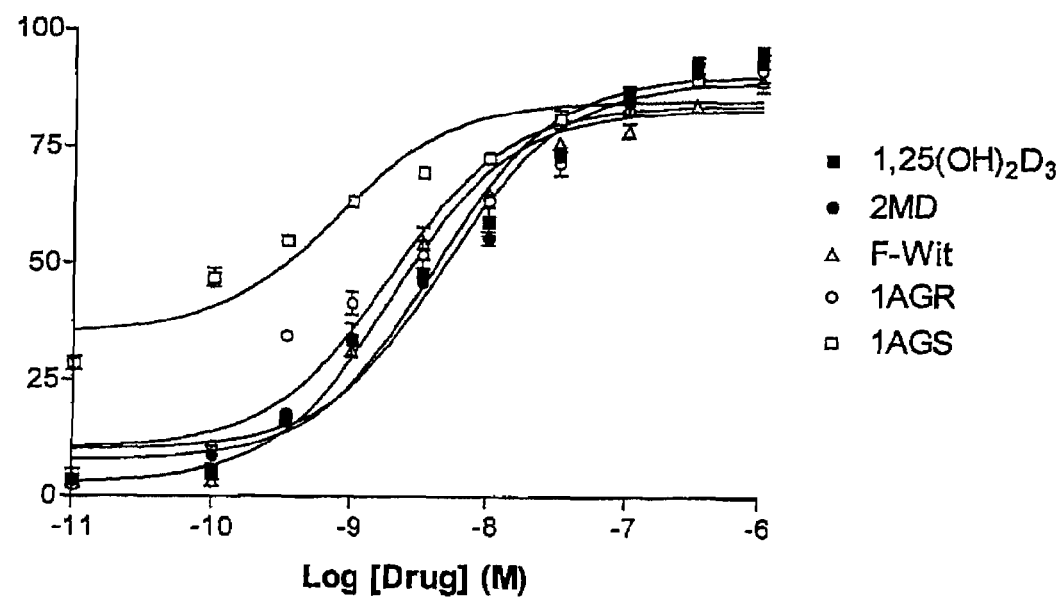
FIG. 3 is a graph illustrating the percent HL-60 cell differentiation as a function of the concentration of 1α,25-dihydroxyvitamin $D_3$, (20S)-2-methylene-19-nor-1α,25-dihydroxyvitamin $D_3$ (2MD) and the herein described and claimed 2-[(3'-methoxymethoxy)propylidene]-19-nor-1α,25-$(OH)_2D_3$ (F-Wit), the E-isomer of 2-(3'-hydroxypropylidene)-19-nor-1α,25-$(OH)_2D_3$ (1AGR), and the E-isomer of 2-(3'-hydroxypropylidene)-19-nor-(20S)1α,25-$(OH)_2D_3$ (1AGS)

FIG. 3—HL-60 Cell Differentiation

The differentiation of HL-60 promyelocytic into monocytes was determined as described by Ostrem et al (J. Biol. Chem. 262, 14164-14171, 1987).

Figure 4:
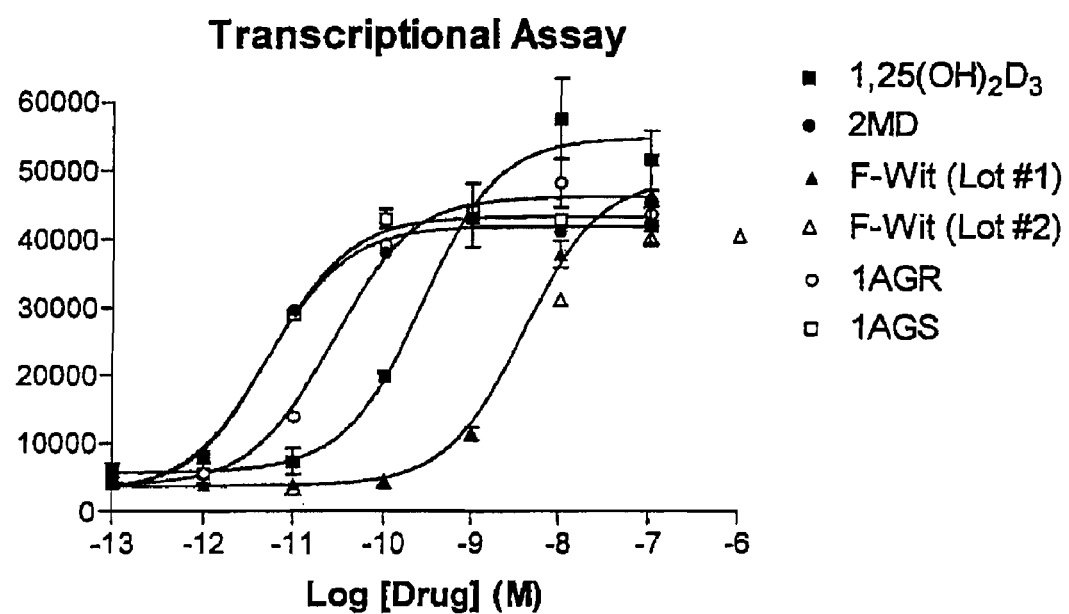
FIG. 4 is a graph illustrating the transcriptional activity as a function of the concentration of 1α,25-dihydroxyvitamin, (20S)-2-methylene-19-nor-1α,25-dihydroxyvitamin $D_3$ (2MD) and the herein described and claimed 2-[(3'-methoxymethoxy)propylidene]-19-nor-1α,25-$(OH)_2D_3$ (F-Wit), the E-isomer of 2-(3'-hydroxypropylidene)-19-nor-1α,25-$(OH)_2D_3$ (1AGR), and the E-isomer of 2-(3'-hydroxypropylidene)-19-nor-(20S)-1α,25-$(OH)_2D_3$ (1AGS)

FIG. 4—Transcription Activation

Transcriptional activity was measured in ROS 17/2.8 (bone) cells that were stably transfected with a 24-hydroxylase (24OHase) gene promoter upstream of a luciferase reporter gene (Arbour et al., 1998). Cells were given a range of doses. Sixteen hours after dosing the cells were harvested and luciferase activities were measured using a luminometer. "RLU" in FIG. 4 refers to relative luciferase units.

Figure 5:
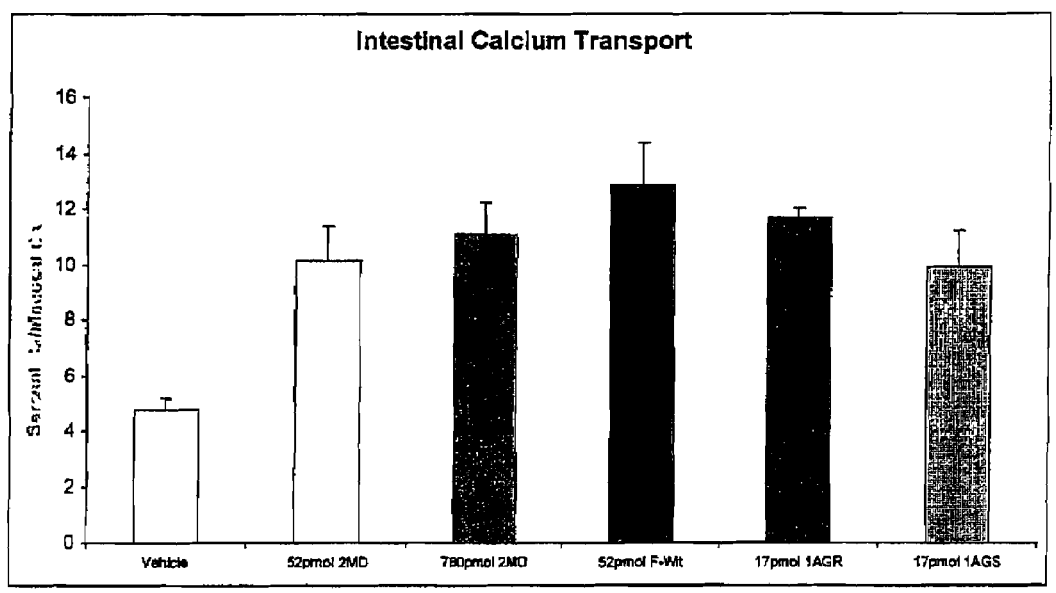
FIG. 5 is a bar graph illustrating the intestinal calcium transport activity of 2-[(3'-methoxymethoxy)propylidene]-19-nor-1α,25-$(OH)_2D_3$ (F-Wit), the E-isomer of 2-(3'-hydroxypropylidene)-19-nor-1α,25-$(OH)_2D_3$ (1AGR), and the E-isomer of 2-(3'-hydroxypropylidene)-19-nor-(20S)-1α,25-$(OH)_2D_3$ (1AGS) at various dosages as compared to control (vehicle) and (20S)-2-methylene-19-nor-1α,25-dihydroxyvitamin $D_3$ (2MD)
Figure 6:
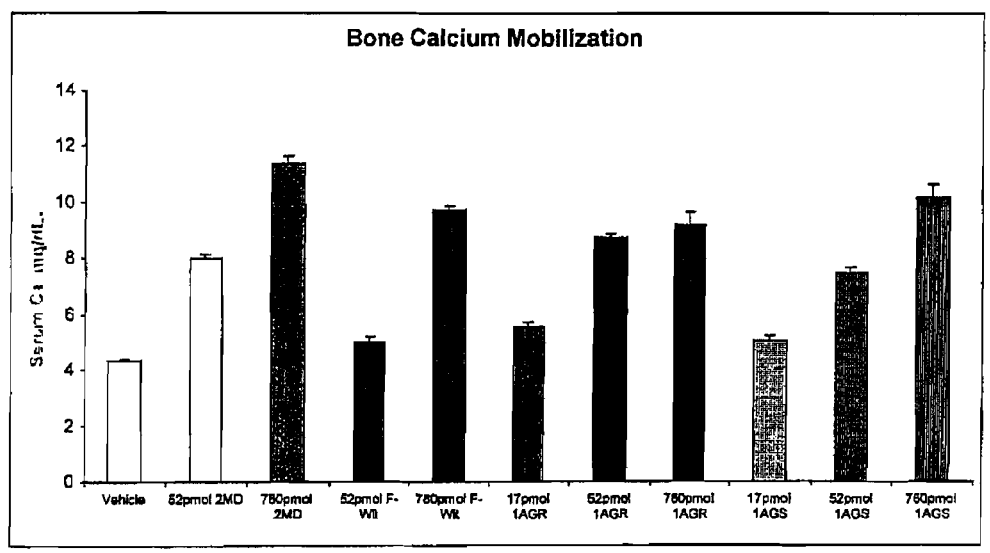
FIG. 6 is a bar graph illustrating the bone calcium mobilization activity of 2-[(3'-methoxymethoxy)propylidene]-19-nor-1α,25-$(OH)_2D_3$ (F-Wit), the E-isomer of 2-(3'-hydroxypropylidene)-19-nor-1α,25-$(OH)_2D_3$ (1AGR), and the E-isomer of 2-(3'-hydroxypropylidene)-19-nor-(20S)-1α,25-$(OH)_2D_3$ (1AGS) at various dosages as compared to control (vehicle) and (20S)-2-methylene-19-nor-1α,25-dihydroxyvitamin $D_3$ (2MD).

FIGS. 5 and 6—Intestinal Calcium Transport and Bone Calcium Mobilization Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

Interpretation of Biological Data

FIG. 1 illustrates the relative activity of 2-[(3'-methoxymethoxy)propylidene]-19-nor-1α,25-(OH)$_2$D$_3$ (also herein referred to as "F-Wit") and 1α,25-dihydroxyvitamin D$_3$ in binding to the 1α,25-dihydroxyvitamin D pig intestinal nuclear receptor. FIG. 2 illustrates the relative activity of the E-isomer of 2-(3'-hydroxypropylidene)-19-nor-1α,25-(OH)$_2$D$_3$ (also herein referred to as "1AGR"), the Z-isomer of 2-(3'-hydroxypropylidene)-19-nor-1α,25-(OH)$_2$D$_3$ (also herein referred to as "2AGR"), the E-isomer of 2-(3'-hydroxypropylidene)-19-nor-(20S)-1α,25-(OH)$_2$D$_3$ (also herein referred to as "1AGS"), the Z-isomer of 2-(3'-hydroxypropylidene)-19-nor-(20S)-1α,25-(OH)$_2$D$_3$ (also herein referred to as "2AGS"), and 1α,25-dihydroxyvitamin D$_3$ in binding to the 1α,25-dihydroxyvitamin D pig intestinal nuclear receptor. FIGS. 1 and 2 show that F-Wit, 1AGR, 2AGR, 1AGS and 2AGS are all very active in binding to the 1α,25-hydroxyvitamin D$_3$ rat receptor.

The 2-propylidene-19-nor compounds of this invention exhibit a pattern of biological activity having high potency in promoting the differentiation of malignant cells, relatively high intestinal calcium transport activity and a relatively high ability to mobilize calcium from bone. This is illustrated by the biological assay results obtained for F-Wit, 1AGR, 2AGR, 1AGS and 2AGS which is summarized in FIGS. 3 through 6. FIG. 3 shows a comparison of the activity of the known active metabolite 1α,25-dihydroxyvitamin D$_3$ as well as the analog 2-methylene-19-nor-(20S)-1,25(OH)$_2$D$_3$ (also herein referred to as "2MD") and the presently claimed F-Wit, 1AGR and 1AGS analogs in inducing the differentiation of human leukemia cells (HL-60 cells) in culture to monocytes. Differentiation activity was assessed by a standard differentiation assay, abbreviated as NBT reduction (nitroblue tetrazolium reduction). The assay was conducted according to known procedures, as given, for example, by DeLuca et al U.S. Pat. No. 4,717,721 and Ostrem et al, J. Biol. Chem. 262, 14164, 1987. For the assay, the differentiation activity of the test compounds is expressed in terms of the percent of HL-60 cells having differentiated to normal cells in response to a given concentration of test compound.

The results summarized in FIG. 3 clearly show that the analogs, F-Wit, 1AGR and 1AGS are all as potent as 1α,25-dihydroxyvitamin D$_3$ and 2MD in promoting the differentiation of leukemia cells. Thus, in the NBT assay close to 90% of the cells are induced to differentiate by 1α,25-dihydroxyvitamin D$_3$ at a concentration of 1×10$^{-7}$M, and the same degree of differentiation is achieved by the F-Wit, 1AGR and 1AGS analogs at 1×10$^{-7}$M.

FIG. 4 illustrates that F-Wit, 1AGR and 1AGS all have significant transcriptional activity in bone cells. This result, together with the cell differentiation activity of FIG. 3, suggests that the presently claimed 2-propylidene compounds of structure I, and particularly F-Wit, 1AGR and 1AGS, will be very effective in psoriasis because they have direct cellular activity in causing cell differentiation and in suppressing cell growth. These data also indicate that the presently claimed 2-propylidene compounds of structure I, and particularly F-Wit, 1AGR and 1AGS may have significant activity as an anti-cancer agent, especially against leukemia, colon cancer, breast cancer, skin cancer and prostate cancer.

FIGS. 5 and 6 show a comparison of the calcemic activity of the known active 19-nor analog 2MD and the presently claimed F-Wit, 1AGR and 1AGS analogs. FIG. 5 shows that F-Wit, 1AGR and 1AGS all have relatively high intestinal calcium transport activity, and are more active than 2MD in intestinal calcium transport activity. Also, FIG. 6 shows that F-Wit, 1AGR and 1AGS all have significant ability to mobilize calcium from bone, and are less active in this regard than 2MD. Thus, in summary, the 2-propylidene-19-nor-analogs of structure I, and particularly F-Wit, 1AGR and 1AGS, show a selective activity profile combining high potency in inducing the differentiation of malignant cells, relatively high intestinal calcium transport activity and moderate bone calcium mobilization activity.

The invention claimed is:

1. A compound having the formula:

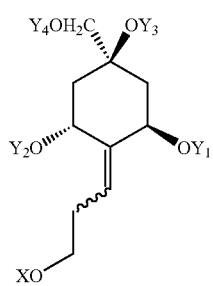

where Y$_1$, Y$_2$, Y$_3$ and Y$_4$, which may be the same or different, are each selected from the group consisting of hydrogen and a hydroxy-protecting group, and where X may be an alkyl, hydrogen, hydroxy-protecting group, hydroxyalkyl, alkoxyalkyl and aryloxyalkyl.

2. A compound having the formula:

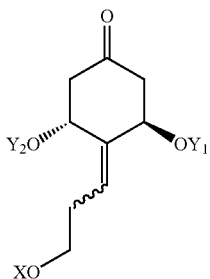

where $Y_1$ and $Y_2$, which may be the same or different, are each selected from the group consisting of hydrogen and a hydroxy-protecting group, and where X may be an alkyl, hydrogen, hydroxy-protecting group, hydroxyalkyl, alkoxyalkyl and aryloxyalkyl.

3. A compound having the formula:

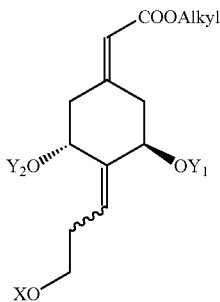

where $Y_1$ and $Y_2$, which may be the same or different, are each selected from the group consisting of hydrogen and a hydroxy-protecting group, and where X may be an alkyl, hydrogen, hydroxy-protecting group, hydroxyalkyl, alkoxyalkyl and aryloxyalkyl.

4. A compound having the formula:

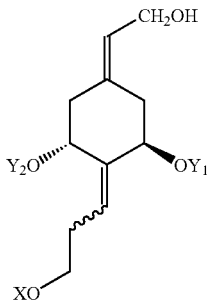

where $Y_1$ and $Y_2$, which may be the same or different, are each selected from the group consisting of hydrogen and a hydroxy-protecting group, and where X may be an alkyl, hydrogen, hydroxy-protecting group, hydroxyalkyl, alkoxyalkyl and aryloxyalkyl.

5. A compound having the formula:

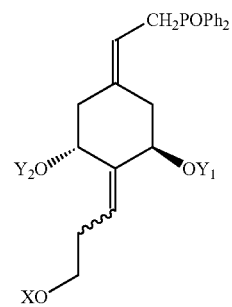

where $Y_1$ and $Y_2$, which may be the same or different, are each selected from the group consisting of hydrogen and hydroxy-protecting group, and where X may be an alkyl, hydrogen, hydroxy-protecting group, hydroxyalkyl, alkoxyalkyl and aryloxyalkyl.

6. A compound having the formula:

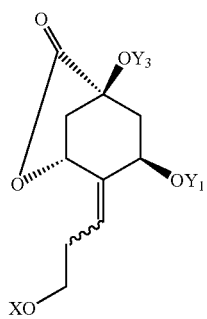

where $Y_1$ and $Y_3$, which may be the same or different, are each selected from the group consisting of hydrogen and a hydroxy-protecting group, and where X may be an alkyl, hydrogen, hydroxy-protecting group, hydroxyalkyl, alkoxyalkyl and aryloxyalkyl.

* * * * *